(12) United States Patent
Powell, Jr. et al.

(10) Patent No.: US 9,272,002 B2
(45) Date of Patent: Mar. 1, 2016

(54) FULLY HUMAN, ANTI-MESOTHELIN SPECIFIC CHIMERIC IMMUNE RECEPTOR FOR REDIRECTED MESOTHELIN-EXPRESSING CELL TARGETING

(71) Applicant: THE TRUSTEES OF THE UNIVERSITY OF PENNSYLVANIA, Philadelphia, PA (US)

(72) Inventors: Daniel J. Powell, Jr., Bala Cynwyd, PA (US); Nathalie Scholler, Mountain View, CA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 14/354,171

(22) PCT Filed: Oct. 26, 2012

(86) PCT No.: PCT/US2012/062159
§ 371 (c)(1),
(2) Date: Apr. 25, 2014

(87) PCT Pub. No.: WO2013/063419
PCT Pub. Date: May 2, 2013

(65) Prior Publication Data
US 2014/0301993 A1 Oct. 9, 2014

Related U.S. Application Data

(60) Provisional application No. 61/552,820, filed on Oct. 28, 2011.

(51) Int. Cl.
*A61K 48/00* (2006.01)
*A61K 35/17* (2015.01)
*C07K 16/28* (2006.01)
*C07K 14/725* (2006.01)

(52) U.S. Cl.
CPC ............. *A61K 35/17* (2013.01); *C07K 14/7051* (2013.01); *C07K 16/28* (2013.01); *A61K 48/005* (2013.01); *C07K 2319/33* (2013.01); *C07K 2319/75* (2013.01); *C12N 2799/027* (2013.01)

(58) Field of Classification Search
None
See application file for complete search history.

(56) References Cited

U.S. PATENT DOCUMENTS

| | | | |
|---|---|---|---|
| 4,444,887 A | 4/1984 | Hoffmann | |
| 4,694,778 A | 9/1987 | Learn et al. | |
| 4,716,111 A | 12/1987 | Osband et al. | |
| 4,816,567 A | 3/1989 | Cabilly et al. | |
| 5,199,942 A | 4/1993 | Gillis | |
| 5,225,539 A | 7/1993 | Winter | |
| 5,229,275 A | 7/1993 | Goroff | |
| 5,350,674 A | 9/1994 | Boenisch et al. | |
| 5,413,923 A | 5/1995 | Kucherlapati et al. | |
| 5,530,101 A | 6/1996 | Queen et al. | |
| 5,545,806 A | 8/1996 | Lonberg et al. | |
| 5,565,332 A | 10/1996 | Hoogenboom et al. | |
| 5,567,610 A | 10/1996 | Borrebaeck et al. | |
| 5,569,825 A | 10/1996 | Lonberg et al. | |
| 5,573,905 A | 11/1996 | Lerner et al. | |
| 5,585,089 A | 12/1996 | Queen et al. | |
| 5,585,362 A | 12/1996 | Wilson et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,766,886 A | 6/1998 | Studnicka et al. | |
| 5,814,318 A | 9/1998 | Lonberg et al. | |
| 5,858,358 A | 1/1999 | June et al. | |
| 5,883,223 A | 3/1999 | Gray | |
| 5,939,598 A | 8/1999 | Kucherlapati et al. | |
| 5,993,434 A | 11/1999 | Dev et al. | |
| 6,120,766 A | 9/2000 | Hale et al. | |
| 6,181,964 B1 | 1/2001 | Hofmann et al. | |
| 6,233,482 B1 | 5/2001 | Hofmann et al. | |
| 6,241,701 B1 | 6/2001 | Hofmann | |
| 6,326,193 B1 | 12/2001 | Liu et al. | |
| 6,331,415 B1 | 12/2001 | Cabilly et al. | |
| 6,352,694 B1 | 3/2002 | June et al. | |
| 6,407,213 B1 | 6/2002 | Carter et al. | |
| 6,516,223 B2 | 2/2003 | Hofmann | |
| 6,534,055 B1 | 3/2003 | June et al. | |
| 6,548,640 B1 | 4/2003 | Winter | |
| 6,678,556 B1 | 1/2004 | Nolen et al. | |

(Continued)

FOREIGN PATENT DOCUMENTS

EP 0239400 9/1987
EP 0519596 12/1992

(Continued)

OTHER PUBLICATIONS

Alvarez-Vallina, et al., "Antigen-specific targeting of CD28-mediated T cell co-stimulation using chimeric single-chain antibody variable fragment-CD28 receptors", Eur. J. Immunol., 26:2304-2309 (1996).

(Continued)

*Primary Examiner* — Janice Li
(74) *Attorney, Agent, or Firm* — Saul Ewing LLP; Kathryn Doyle; Kelly J. Morgan

(57) ABSTRACT

The present invention relates to compositions and methods for treating diseases, disorders or conditions associated with dysregulated expression of mesothelin. In one embodiment, the invention relates to a fully human chimeric antigen receptor (CAR) wherein the CAR is able to target mesothelin.

13 Claims, 21 Drawing Sheets

(56) References Cited

U.S. PATENT DOCUMENTS

| | | | |
|---|---|---|---|
| 6,692,964 | B1 | 2/2004 | June et al. |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,067,318 | B2 | 6/2006 | June et al. |
| 7,144,575 | B2 | 12/2006 | June et al. |
| 7,171,264 | B1 | 1/2007 | Hofmann et al. |
| 7,172,869 | B2 | 2/2007 | June et al. |
| 7,173,116 | B2 | 2/2007 | Fewell et al. |
| 7,175,843 | B2 | 2/2007 | June et al. |
| 7,232,566 | B2 | 6/2007 | June et al. |
| 7,943,133 | B2 * | 5/2011 | Gelfand ............... 424/134.1 |
| 8,211,422 | B2 * | 7/2012 | Eshhar et al. .......... 424/93.21 |
| 8,906,682 | B2 * | 12/2014 | June et al. ............. 435/372.3 |
| 2004/0014645 | A1 | 1/2004 | Draghia-Akli et al. |
| 2004/0059285 | A1 | 3/2004 | Mathiesen et al. |
| 2004/0092907 | A1 | 5/2004 | Mathiesen et al. |
| 2004/0101519 | A1 | 5/2004 | June et al. |
| 2005/0042664 | A1 | 2/2005 | Wu et al. |
| 2005/0048617 | A1 | 3/2005 | Wu et al. |
| 2005/0052630 | A1 | 3/2005 | Smith et al. |
| 2005/0070841 | A1 | 3/2005 | Mathiesen et al. |
| 2006/0034810 | A1 | 2/2006 | Riley et al. |
| 2006/0121005 | A1 | 6/2006 | Berenson et al. |
| 2007/0128708 | A1 | 6/2007 | Gamelin |
| 2009/0257991 | A1 | 10/2009 | Li et al. |
| 2010/0178276 | A1 | 7/2010 | Sadelain et al. |
| 2014/0099309 | A1 * | 4/2014 | Powell et al. ............ 424/135.1 |

FOREIGN PATENT DOCUMENTS

| | | |
|---|---|---|
| EP | 0592106 | 4/1994 |
| WO | WO91/09967 | 7/1991 |
| WO | WO91/10741 | 7/1991 |
| WO | WO93/17105 | 9/1993 |
| WO | WO96/33735 | 10/1996 |
| WO | WO96/34096 | 10/1996 |
| WO | WO98/16654 | 4/1998 |
| WO | WO98/24893 | 6/1998 |
| WO | WO98/46645 | 10/1998 |
| WO | WO98/50433 | 11/1998 |
| WO | WO01/29058 | 4/2001 |
| WO | WO01/96584 | 12/2001 |

OTHER PUBLICATIONS

Argani, et al., "Mesothelin is Overexpressed in the Vast Majority of Ductal Adenocarcinomas of the Pancreas: Indentification of a New Pancreatic Cancer Marker by Serial Analysis of Gene Expression (SAGE)$_1$", Clin. Cancer Res., 7:3862-3868 (2001).

Baca et al., "Antibody Humanization Using Monovalent Phage Display", The Journal of Biological Chemistry, 272:10678-10684 (1997).

Beecham, et al., "Coupling CD28 co-stimulation to immunoglobulin T-cell receptor molecules: the dynamics of T-cell proliferation and death", J Immunother., 23(6):631-642 (2000).

Bergan et al., "Development and in vitro validation of anti-mesothelin biobodies that prevent CA125/Mesothelin-dependent cell attachment", Cancer Letters, 255:263-274 (2007).

Betts, et al., "Sensitive and viable identification of antigen-specific CD8+ T cells by a flow cytometric assay for degranulation", J. Immunol. Methods 281(1-2):65-78 (2003).

Bierer et al., "Cyclosporine A and FK506: molecular mechanisms of immunosuppression and probes for transplantation biology", Current Opinion in Immunology 5:763-773 (1993).

Bird et al., "Single-Chain Antigen-Binding Proteins", Science, New Series 242(4877):423-426 (1988).

Brüggemann et al., "Designer Mice: The Production of Human Antibody Repertoires in Transgenic Animals", Generation of Antibodies by Cell and Gene Immortalization, 7:33-40 (1993).

Caldas et al., "Design and synthesis of germline-based hemi-humanized single-chain Fv against the CD18 surface antigen", Protein Engineering, 13(5):353-360 (2000).

Carpenito et al., "Control of large, established tumor xenografts with genetically retargeted human T cells containing CD28 and CD137 domains", PNAS, 106(9):3360-3365 (2009).

Carter et al., "Humanization of an anti-p185$^{HER2}$ antibody for human cancer therapy", Proc. Natl. Acad. Sci., 89:4285-4289 (1992).

Chang, et al., "Molecular cloning of mesothelin, a differentiation antigen present on mesothelium, mesotheliomas, and ovarian cancers", Proc. Natl. Acad. Sci., 93:136-140 (1996).

Cheng et al., "Overexpression of B7-H4 in tumor infiltrated dendritic cells", Journal of Immunoassay and Immunochemistry, 32(4):353-364 (2011).

Chothia et al., "Canonical Structures for the Hypervariable Regions of Immunoglobulins", J. Mol. Biol., 196:901-917 (1987).

Chowdhury, et al., "Isolation of a high-affinity stable single-chain Fv specific for mesothelin from DNA-immunized mice by phage display and construction of a recombinant immunotoxin with anti-tumor activity", Proc. Natl. Acad. Sci., 95:669-674 (1998).

Clackson et al., "Making antibody fragments using phage display libraries", Nature, 352:624-628 (1991).

Couto et al., "Designing Human Consensus Antibodies with Minimal Positional Templates", Cancer Research, 55:5973s-5977s (1995).

Cuoto et al., "Anti-BA46 Monoclonal Antibody Mc3: Humanization Using a Novel Positional Consensus and in Vivo Characterization", Cancer Research, 55:1717-1722 (1995).

Duchosal et al., "Immunization of hu-PBL-SCID mice and the rescue of human monoclonal Fab fragments through combinatorial libraries", Nature, 355:258-262 (1992).

Feldhaus, et al., "A CD2/CD28 chimeric receptor triggers the CD28 signaling pathway in CTLL.2 cells", Gene Therapy, 4:833-838 (1997).

Garland et al., "The use of Teflon cell culture bags to expand functionally active CD8+ cytotoxic T lymphocytes", Journal of Immunological Methods, 227:53-63 (1999).

Griffiths et al., "Human anti-self antibodies with high specificity from phage display libraries", The EMBO Journal, 12(2):725-734 (1993).

Gross, et al., "Expression of immunoglobulin-T-cell receptor chimeric molecules as functional receptors with antibody-type specificity", Proc. Natl. Acad. Sci., 86:10024-10028 (1989).

Haanen et al., "Selective Expansion of Cross-reactive CD8+ Memory T Cells by Viral Variants", J. Exp. Med., 190(9):1319-1328 (1999).

Han, et al., "HLA Class I Antigen Processing Machinery Component Expression and Intratumoral T-Cell Infiltate as Independent Prognostic Markers in Ovarian Carcinoma", Clin. Cancer Res., 14(11):3372-3379 (2008).

Hassan, et al., "Detection and Quantitation of Serum Mesothelin, a tumor Marker for Patients with Medothelioma and Ovarian Cancer", Clin. Cancer Res., 12(2):447-453 (2006).

Hassan, et al., "Phase I Study of SS1P, a Recombinant Anti-Mesothelin Immunotoxin Given as a Bolus I.V. Infusion to Patients with Mesothelin-Expressing Mesothelioma, Ovarian, and Pancreatic Cancers", Clin. Cancer Res., 13(17):5144-5149 (2007).

Hellstrom, "Mesothelin in serum", Biochem. Biophys. Res. Commun., 376:629 (2008).

Henderson et al., "Comparison of the effects of FK-506, cyclosporin A and rapamycin on IL-2 production", Immunology, 73:316-321 (1991).

Ho, et al., "Mesothelin Expression in Human Lung Cancer", Clin. Cancer Res., 13(5):1571-1575 (2007).

Hombach, et al., "T-Cell Activation by Recombinant Receptors: CD28 Costimulation is Required for Interleukin 2 Secretion and Receptor-mediated T-Cell Proliferation but Does Not Affect Receptor-mediated Target Cell Lysis", Cancer Research, 61:1976-1982 (2001).

Hoogenboom et al., "By-Passing immunization. Human antibodies from synthetic repertoires of germline VH gene segments rearranged in vitro", J. Mol. Biol., 227(2):381-388 (1992).

(56) References Cited

OTHER PUBLICATIONS

Huston et al., "Protein engineering of antibody binding sites: Recovery of specific activity in an anti-digoxin single-chain Fv analogue produced in *Escherichia coli*", Proc. Natl. Acad. Sci., 85:5879-5883 (1988).

Jackaman, et al., IL-2 Intratumoral Immunotherapy Enhances CD8 + T Cells That Mediate Destruction of Tumor Cells and Tumor-Associated Vasculature: A Novel Mechanism for IL-2, J. Immunol., 171: 5051-5063 (2003).

Jakobovits et al., "Analysis of homozygous mutant chimeric mice: Deletion of the immunoglobulin heavy-chain joining region blocks B-cell development and antibody production," Proc. Natl. Acad. Sci., 90:2551-2555 (1993).

Jakobovits et al., "Germ-line transmission and expression of a human-derived yeast artificial chromosome", Nature, 362:255-258 (1993).

Jena et al., "Redirection T-cell specificity by introducing a tumor-specific chimeric antigen receptor", Blood, 116(7):1035-1044 (2010).

Johnson et al., "Gene Transfer of Tumor-Reactive TCR Confers Both High Avidity and Tumor Reactivity to Nonreactive Peripheral Blood Mononuclear Cells and Tumor-Infiltrating Lymphochytes", J. Immunol, 177(9):6548-6559 (2006).

Johnson et al., "Human antibody engineering", Current Opinion in Structural Biology, 3:564-571 (1993).

Jones et al., "Replacing the completmentary-determining regions in a human antibody with those from a mouse", Nature, 321:522-525 (1986).

Kaneko, et al., "A Binding Domain on Mesothelin for CA125/MUC16*", J. Biol. Chem., 284(6):3739-3749 (2009).

Kershaw, et al., "A Phase I Study on Adoptive Immunotherapy Using Gene-Modified T Cells for Ovarian Cancer", Clin. Cancer Res., 12(20):6106-6115 (2006).

Kowolik, et al., "CD28 Costimulation Provided through a CD19-Specific Chimeric Antigen Receptor Enhances In vivo Persistence and Antitumor Efficacy of Adoptively Transferred T Cells", Cancer Res., 66(22):10995-11004 (2006).

Kreitman, et al., "Phase I Trial of Continuous Infusion Anti-Mesothelin Recombinant Immunotoxin SS1P", Clin. Cancer Res., 15(16):5274-5279 (2009).

Lamers, et al., "Gene-modified T cells for adoptive immunotherapy of renal cell cancer maintain transgene-specific functions in vivo", Cancer Immunol., Immunother., 56:1875-1883 (2007).

Lamers, et al., "Immune responses to transgene and retroviral vector in patients treated with ex vivo-engineered T cell", Blood, 117(1):72-82 (2011).

Lamers, et al., Treatment of Metastatic Renal Cell Carcinoma With Autologous T-Lymphocytes Genetically Retargeted Against Carbonic Anhydrase IX: First Clinical Expericenc. J. Clin. Oncol., 24(13):e20-22 (2006).

Levine et al., "Effects of CD28 Costimulation on Long-Term Proliferation of CD4+ T Cells in the Absence of Exogenous Feeder Cells[1]", The Journal of Immunology, 159:5921-5930 (1997).

Liu et al., "Calcineurin is a Common Target of Cyclophilin-Cyclosporin A and FKBP-FK506 Complexes", Cell, 66:807-815 (1991).

Lonberg et al., "Human Antibodies from Transgenic Mice", Intern. Rev. Immunol., 13:65-93 (1995).

Mansoor et al., "Engineering T cells for cancer therapy", British Journal of Cancer, 93:1085-1091 (2005).

Marks et al., "By-passing Immunization Human Antibodies from V-gene Libraries Displayed on Phage", J. Mol. Biol., 222:581-597 (1991).

McCafferty et al., "Phage antibodies: filamentous phage displaying antibody variable domains", Nature, 348:552-554 (1990).

Milone, et al., "Chimeric Receptors Containing CD137 Signal Transduction Domains Mediate Enhanced Survival of T Cells and Increased Antileukemic Efficacy In Vivo", Mol. Ther., 17(8): 1453-1464 (2009).

Moon et al., "Expression of a Functional CCR2 Receptor Enhances Tumor Localization and Tumor Eradication by Retargeted Human T cells Expressing a mesothelin-Specific Chimeric Antibody Receptor", Clin. Canc. Res., 17:4719-4730 (2011).

Mumtaz et al., "Design of liposomes for circumventing the reticuloendothelial cells", Glycobiology, 1(5):505-510 (1991).

Nolan, et al., "Bypassing Immunization: Optimized Design of "Designer T Cells", against Carcinoembryonic Antigen (CEA)-expressing Tumors, and Lack of Suppression by Soluble CEA1", Clin. Cancer Res., 5:3928-3941 (1999).

Padlan, "A possible procedure for reducing the immunogenicity of antibody variable domains while preserving their ligand-binding properties", Molecular Immunology, 28(4/5):489-498 (1991).

Park et al., "Adoptive Transfer of Chimeric Antigen Receptor Re-directed Cytolytic T Lymphocyte Clones in Patients with Neuroblastoma", Mol. Ther. 15: 825-833 (2007).

Parkhurst, et al., T Cells Targeting Carcinoembryonic Antigen Can Mediate Regression of Metastatic Colorectal Cancer but Induce Severe Transient Colitis, Mol. Ther., 19(3):620-626 (2011).

Perdersen et al., "Comparison of Surface Accessible Residues in Human and Murine Immunoglobulin Fv Domains, Implications for Humaninzation of Murine Antibodies," J. Mol. Biol., 235:959-973 (1994).

Presta et al., "Humanization of a an Antibody Directed Against IgE", The Journal of Immunology, 151:2623-2632 (1993).

Presta, "Antibody engineering", Current Opinion in Biotechnology, 3:394-398 (1992).

Riechmann et al., "Reshaping human antibodies for therapy", Nature, 332:323-327 (1988).

Robinson, et al., "Soluble mesothelin-related protein—a blood test for mesothelioma", Lung Cancer, 49 (Suppl 1):S109-111 (2005).

Roder et al., "The EBV-Hybridoma Technique", Methods in Enzymology, 121:140-167 (1986).

Roguska et al., "A comparison of two murine monoclonal antibodies humaninzed by CDR-grafting and variable domain resurfing", Protein Engineering, 9(10):895-904 (1996).

Roguska et al., "Humanization of murine monoclonal antibodies through variable domain resurfacing", Proc. Natl. Acad. Sci., 91:969-973 (1994).

Rosenberg et al., "Use of Tumor-Infiltrating Lymphocytes and Interleukin-2 in the Immunotherapy of Patient with Metastatic Melanoma", New Eng. J. of Med., 319(25):1676-1680 (1998).

Rump, et al., "Binding of Ovarian Cancer Antigen CA125/MUC16 to Mesothelin Mediates Cell Adhesion", J. Biol. Chem., 279(10):9190-9198 (2004).

Sandhu, "A rapid procedure for the humanization of monoclonal antibodies", Gene, 150:409-410 (1994).

Scholler et al., "Method for Generation of in vivo Biotinylated Recombinant Antibodies by Yeast Mating", J. Immunol. Methods, 317(1-2):132-143 (2006).

Search report for PCT/US12/62159 dated Jan. 25, 2013.

Sims et al., "A Humanized CD18 Antibody Can Block Function without Cell Destruction", The Journal of Immunology, 151(4):2296-2308 (1993).

Skerra et al., "Assembly of a Functional Immunoglobulin $F_v$ Fragment in *Escherichia coli*", Science, 240:1038-1041 (1988).

Studnicka et al., "Human-engineered monoclonal antibodies retain full specific binding activity by preserving non-CDR complementarity-modulating residues", Protein Engineering, 7(6):805-814 (1994).

Tan et al., ""Superhumanized" Antibodies: Reduction of Immunogenic Potential by Complementarity-Determining Region Grafting with Human Germline Sequences: Application to an Anti-CD28", The Journal of Immunology, 169:1119-1125 (2002).

Ten Berge et al., "Selective Expansion of a Peripheral Blood CD8+ Memory T Cell Subset Expressing Both Granzyme B and $_L$-Selectin During Primary Viral Infection in Renal Allograft Recipients", Transplantation Proceedings 30:3975-3977 (1988).

Thomas, et al., "Mesothelin-specific CD8+ T Cell Responses Provide Evidence of In Vivo Cross-Priming by Antigen-Presenting Cells in Vaccinated Pancreatic Cancer Patients", J. Exp. Med., 200(3):297-306 (2004).

(56) References Cited

OTHER PUBLICATIONS

Turatti, et al., "Highly efficient redirected anti-tumor activity of human lymphocytes transduced with a completely human chimeric immune receptor", J. Gene Med., 7(2):158-170 (2005).
Ui-Tei et al., "Sensitive assay of RNA interference in *Drosophilia* and Chinese hamster cultured cells using firefly luciferase gene as target", FEBS Letters, 479:79-82 (2000).
Vaughan et al., "Human antibodies with sub-nanomolar affinities isolated from a large non-immunized phage library", Nat. Biotechnol., 14(3):309-314 (1996).
Verhoeyen et al., "Reshaping Human Antibodies: Grafting an Antilysozyme Activity", Science, 239(4847):1534-1536 (1988).
Ward et al., "Binding activities of a repertoire of single immunoglobulin variable domains secreted from *Escherichia coli*", Nature, 341:544-546 (1989).
Westwood, et al., "Adoptive transfer of T cells modified with a humanized chimeric receptor gene inhibits growth of Lewis-Y-expressing tumors in mice", PNAS, 102(52):19051-19056 (2005).
Wu et al., "Humanization of a Murine Monoclonal Antibody by Simultaneous Optimization of Framework and CDR Residues", J. Mol. Biol., 294:151-162 (1999).
Yen, et al., "Diffuse Mesothelin Expresseion Correlates with Prolonged Patient survival in Ovarian Serous Carcinoma", Clin. Cancer Res., 12(3):827-831 (2006).

\* cited by examiner

Figure 3A
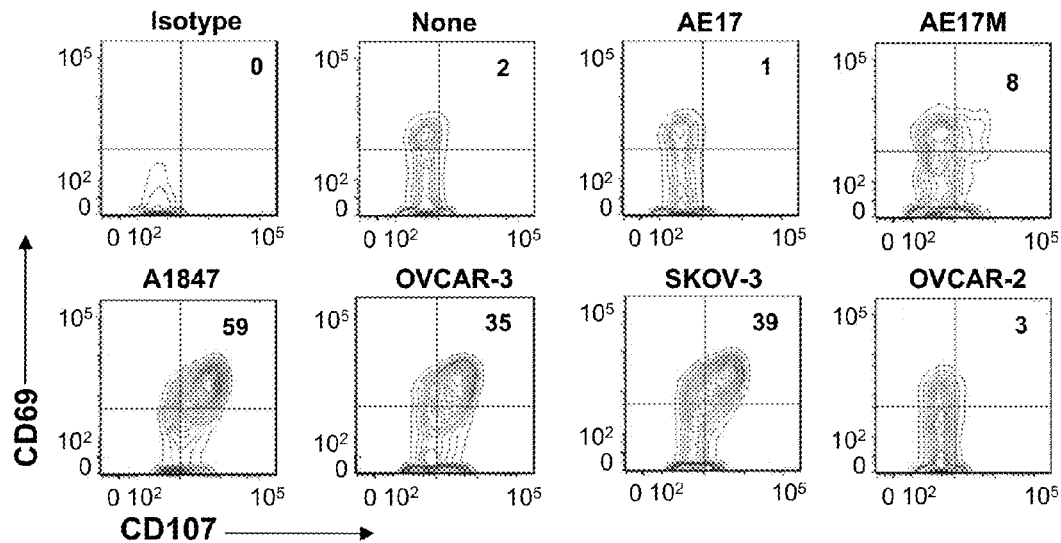
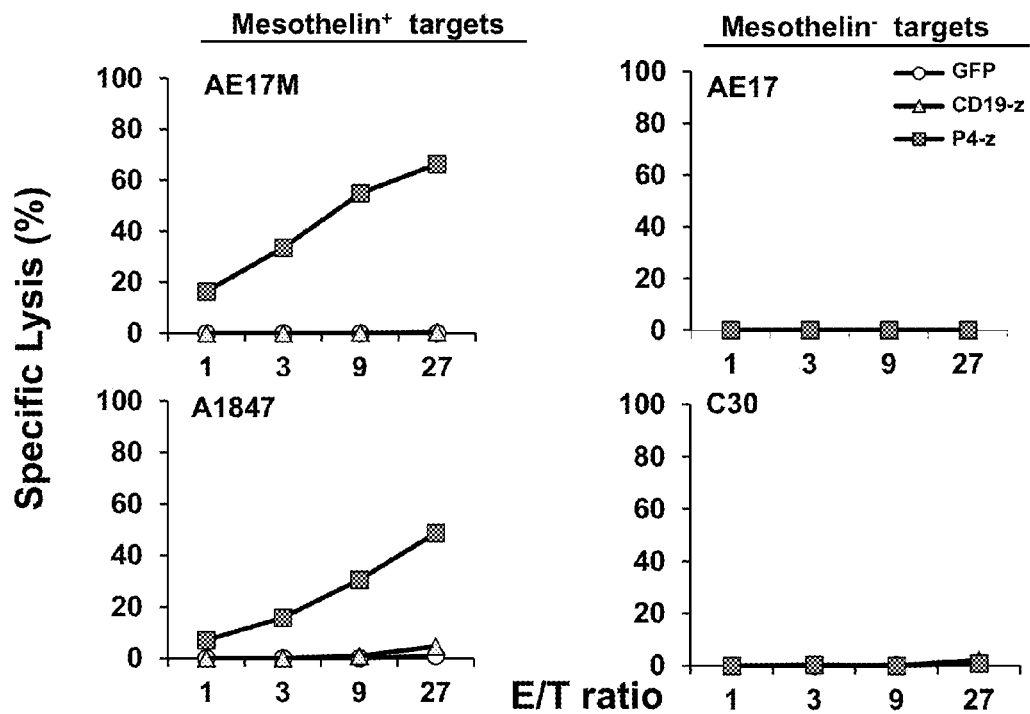
Figure 3B

Figure 6C
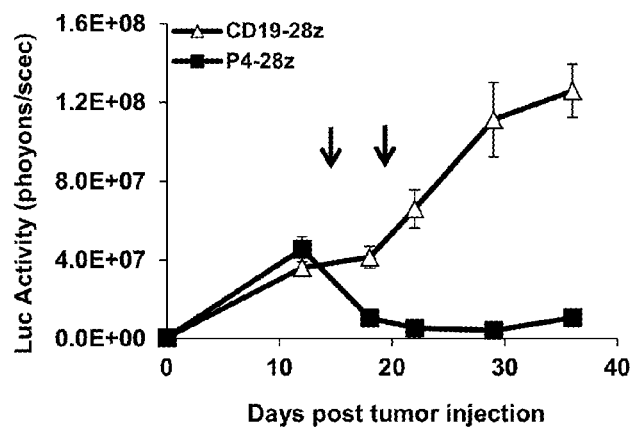
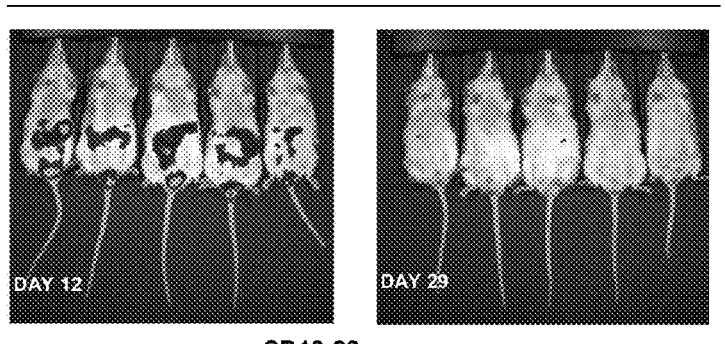
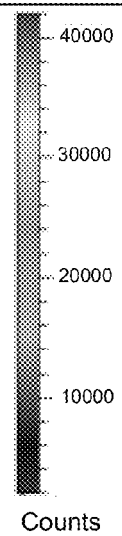
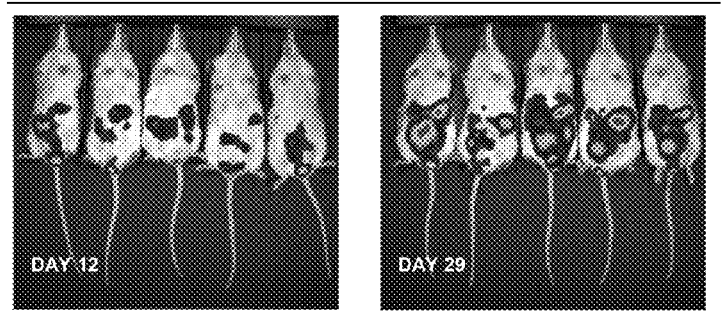
Figure 6D

Figure 6E
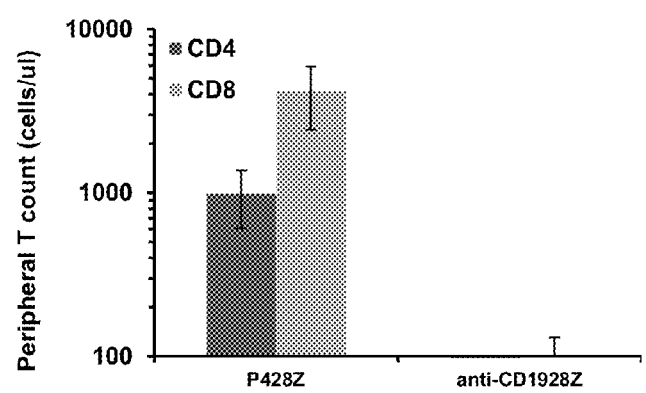
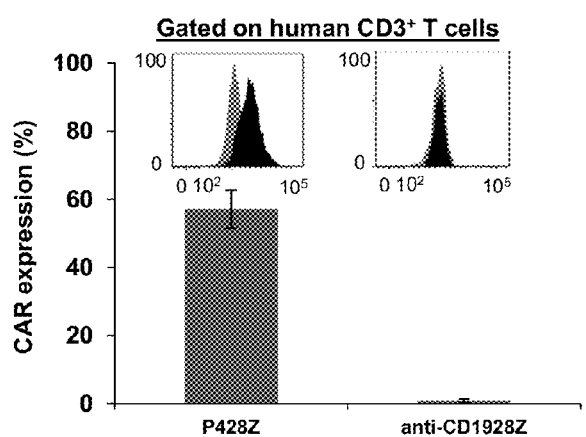
Figure 6F

Figure 11A
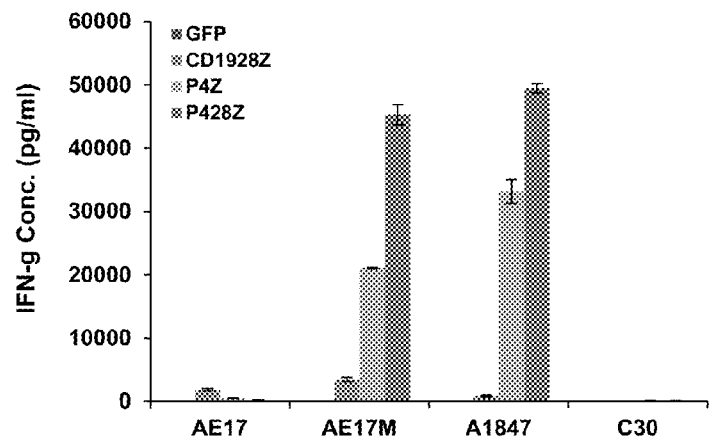
TNF-a
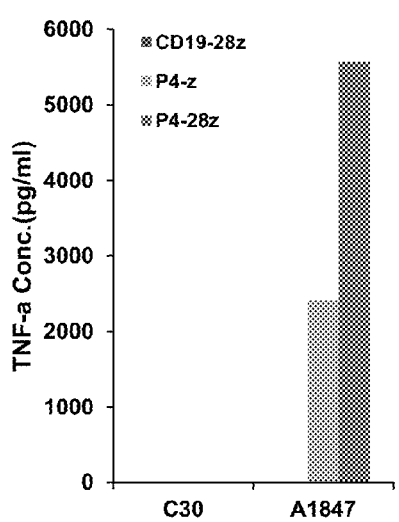
IL-2
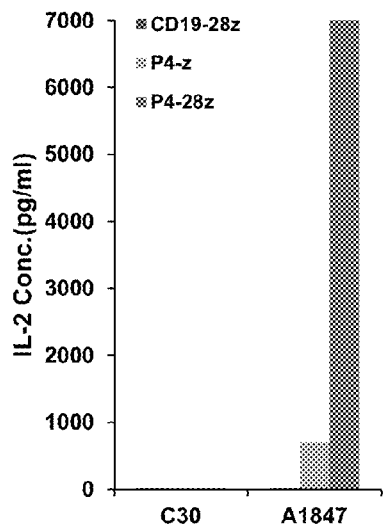
Figure 11B

FULLY HUMAN, ANTI-MESOTHELIN SPECIFIC CHIMERIC IMMUNE RECEPTOR FOR REDIRECTED MESOTHELIN-EXPRESSING CELL TARGETING

CROSS-REFERENCE TO RELATED APPLICATION

This application is the U.S. national phase application filed under 35 U.S.C. §371 claiming benefit to International Patent Application No. PCT/US2012/062159, filed on Oct. 26, 2012, which is entitled to priority under 35 U.S.C. §119(e) to U.S. Provisional Application No. 61/552,820, filed Oct. 28, 2011, each of which is hereby incorporated by reference in its entirety.

BACKGROUND OF THE INVENTION

Successful T cell immunotherapeutic strategies are limited by the tolerance to self-antigens, rendering the identification and expansion of tumor-reactive T cells with high avidity for tumor-associated antigens difficult (Mansoor, et al., 2005, Br J Cancer 93: 1085-1091). Further, solid tumors often down-regulate MHC Class I and/or other molecules related with the antigen processing machinery as a mechanism for evading immune response (Han, et al., 2008, Clin Cancer Res 14: 3372-3379). To obviate these obstacles, tumor antigen-specific T cells have been engineered to express chimeric antigen receptors (CAR)—or "T bodies"—comprised of an antigen-specific single-chain antibody fragment (scFv) fused to intracellular signalling domains derived from receptors involved in lymphocyte activation (Gross, et al., 1989, Proc Natl Acad Sci USA 86: 10024-10028). CARs can functionally redirect T cells with high specificity to various surface antigens on tumor cells independent of MHC restriction and antigen processing, and therefore bypass major mechanisms by which tumors escape immune recognition.

CARs targeting various tumor-associated antigens have been developed, characterized and tested (Jena, et al., 2010, Blood 116: 1035-1044). Despite encouraging pre-clinical results, CAR therapy has had limited success in the clinic primarily due to poor long-term persistence of the engineered T cells following infusion to patients. This may be attributed in part to the frequent use of scFvs of mouse origin which renders these constructs susceptible to host immune recognition and responses against xenogeneic regions of the molecule. Xenogeneic responses have been observed in clinical trials of CAR therapy. For example, patients who received autologous T cells transduced to express a CAR of mouse origin mounted humoral immune responses against the transgene bearing cells, which may have limited their persistence in vivo and their ability to respond against antigen-expressing tumor cells (Kershaw, et al., 2006, Clin Cancer Res 12: 6106-6115; Park, et al., 2007, Mol Ther 15: 825-833).

Mesothelin is a glycosylphosphatidyl inositol-linked membrane glycoprotein overexpressed on the cell surface of mesothelioma, ovarian cancer as well as cancers of the pancreas, stomach and lung (Chang, et al., 1996, Proc Natl Acad Sci USA 93: 136-140; Ho, et al., 2007, Clin Cancer Res 13: 1571-1575; Argani, et al., 2001, Clin Cancer Res 7: 3862-3868). Mesothelin also exists as a soluble form and is a serum biomarker for lung, mesothelioma and ovarian cancer (Scholler, et al., 1999, Proc Natl Acad Sci USA 96: 11531-11536; Hassan, et al., 2006, Clin Cancer Res 12: 447-453; Robinson, et al., 2005, Lung Cancer 49 Suppl 1: S109-111). The biological function of mesothelin is still unclear; however mesothelin binds to CA125, a plasma glycoprotein on tumor cells, suggesting that mesothelin may contribute to peritoneal and pleural metastasis (Kaneko, et al., 2009, J Biol Chem 284: 3739-3749; Rump, et al., 2004, J Biol Chem 279: 9190-9198). Mesothelin expression is associated with chemoresistance, shorter disease-free survival and worse overall survival of patients with epithelial ovarian cancer (EOC) (Cheng, et al., 2009, Br J Cancer 100: 1144-1153). Accordingly, mesothelin represents an attractive target for immune-based therapies. While vaccination with granulocyte macrophage-colony stimulating factor-transduced pancreatic cancer lines can induce in vivo mesothelin-specific $CD8^+$ T cells, with the capacity to kill mesothelin-expressing cancer cells in an MHC Class I-restricted fashion (Thomas, et al., 2004, J Exp Med 200: 297-306), more recent work has shown that human T cells bearing an anti-human mesothelin CAR of mouse origin (referred to as SS1) exhibit MHC-independent effector functions in vitro and induce the regression of human mesothelioma xenografts in vivo in immunodeficient mice (Carpenito, et al., 2009, Proc Natl Acad Sci USA 106: 3360-3365).

Thus, there is an urgent need in the art for compositions and methods for treatment of diseases, disorders or conditions associated with dysregulated expression of mesothelin. The present invention addresses this need.

SUMMARY OF THE INVENTION

The present invention provides an isolated nucleic acid sequence encoding a chimeric antigen receptor (CAR), wherein the isolated nucleic acid sequence comprises the sequence of a human mesothelin binding domain and the sequence of a CD3 zeta signaling domain.

In one embodiment, the isolated nucleic acid sequence further comprises the sequence of a co-stimulatory signaling domain.

In one embodiment, the co-stimulatory signaling domain is selected from the group consisting of CD28 signaling domain and 4-1BB signaling domain.

In one embodiment, the human mesothelin binding domain is a human antibody or a fragment thereof.

In one embodiment, the isolated nucleic acid sequence comprises the nucleic acid sequence selected from the group consisting of SEQ ID NO: 4, SEQ ID NO: 6, and SEQ ID NO: 8.

In one embodiment, the isolated nucleic acid encodes a CAR comprising the amino acid sequence selected from the group consisting of SEQ ID NO: 3, SEQ ID NO: 5, and SEQ ID NO: 7.

The invention also provides an isolated chimeric antigen receptor (CAR) comprising a human mesothelin binding domain and a CD3 zeta signaling domain.

In one embodiment, the isolated CAR further comprises the sequence of a co-stimulatory signaling domain.

In one embodiment, the co-stimulatory signaling domain is selected from the group consisting of CD28 signaling domain and 4-1BB signaling domain.

In one embodiment, the human mesothelin binding domain is a human antibody or a fragment thereof.

In one embodiment, the isolated CAR comprises the amino acid sequence selected from the group consisting of SEQ ID NO: 3, SEQ ID NO: 5, and SEQ ID NO: 7.

The invention comprises a genetically modified cell comprising an isolated nucleic acid sequence encoding a chimeric antigen receptor (CAR), wherein the isolated nucleic acid sequence comprises the sequence of a human mesothelin binding domain and the nucleic acid sequence of a CD3 zeta signaling domain.

In one embodiment, the genetically modified cell is a T cell.

In one embodiment, the genetically modified cell exhibits an anti-tumor immunity when the cell is cross-linked with a mesothelin protein.

The invention also provides a method of providing an anti-tumor immunity in a mammal, the method comprising administering to the mammal an effective amount of a genetically modified cell comprising an isolated nucleic acid sequence encoding a chimeric antigen receptor (CAR), wherein the isolated nucleic acid sequence comprises the sequence of a human mesothelin binding domain and the nucleic acid sequence of a CD3 zeta signaling domain.

In one embodiment, the cell is an autologous T cell.

In one embodiment, the mammal is a human.

The invention also provides a method of treating a mammal having a disease, disorder or condition associated with dysregulated expression of mesothelin, the method comprising administering to the mammal an effective amount of a genetically modified cell comprising an isolated nucleic acid sequence encoding a chimeric antigen receptor (CAR), wherein the isolated nucleic acid sequence comprises the sequence of a human mesothelin binding domain and the nucleic acid sequence of a CD3 zeta signaling domain.

In one embodiment, the disease, disorder or condition associated with dysregulated expression of mesothelin is selected from the group consisting of mesothelioma, pancreatic cancer, ovarian cancer, stomach cancer, lung cancer, endometrial cancer, and any combination thereof.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A is a schematic representation of P4 based Chimeric Antigen Receptor (CAR) constructs containing the CD3z cytosolic domain alone (P4-z) or in combination with the CD28 costimulatory module (P4-28z). The anti-CD19-z and anti-CD19-28z CARs are shown. P4=anti-mesothelin scFv; VL=variable L chain; L=Linker; VH=variable H chain; TM=transmembrane region. FIG. 1B is an image demonstrating that P4 CAR expression (filled black histograms) was detected on human CD3-gated cells via recombinant mesothelin protein staining after transduction with lentivirus compared to untransduced T cells (open histograms). Anti-CD19 transduced T cells were detected using polyclonal goat anti-mouse Ig antibody. Transduction efficiencies are indicated with the percentage of CAR expression and the mean fluorescence intensity of the transduced populations in parentheses.

FIG. 2, comprising FIG. 2A is an image demonstrating that transduced T cells respond against immobilized but not soluble mesothelin. P4-z T cells or control anti-CD19-z and GFP T cells ($10^5$ cells/well) were incubated with either 5 ug/ml of soluble or plate-immobilized mesothelin. After overnight incubation, culture supernatants were analyzed for human Th1/Th2 cytokines using cytometric bead array technology. Concentration of IFN-γ was expressed in pg/ml. FIG. 2B is an image demonstrating that surface mesothelin expression (solid black histograms) by various human ovarian cancer cell lines was evaluated by flow cytometry. The native mouse malignant mesothelioma cell line AE17 which does not express human mesothelin was engineered to express high surface levels of human mesothelin (AE17M) as shown by flow cytometry; isotype antibody control (open gray histograms). FIG. 2C is an image demonstrating that primary human T cells transduced with P4-z preferentially produce Th1 cytokines after stimulation with mesothelin$^+$ cancer cell lines. Transduced T cells ($10^5$ CAR$^+$ T cells) were cultured alone (none) or stimulated overnight with an equal number of human mesothelin AE17M and A1847 or antigen-negative AE17 and C30 cancer cell lines. Cell-free supernatant from three independent cultures was harvested and pooled after ~20 hours of incubation and the indicated human Th1/Th2 cytokines were quantified using cytometric bead array technology. Values represent cytokine concentration (pg/ml). FIG. 2D is an image demonstrating that antigen-stimulated IFN-γ secretion by P4-z but not anti-CD19-z or GFP T cells following overnight incubation with ovarian cancer cell lines expressing different levels of surface mesothelin. Mean IFN-γ concentration±SEM (pg/ml) from triplicate cultures is shown. FIG. 2E is an image demonstrating that correlation of mesothelin expression (mean fluorescence intensity; MFI) on mesothelin-expressing tumor cells was plotted vs. the production of IFN-γ by P4-z CAR-transduced T cells co-cultured with these tumor cells.

FIG. 3, comprising FIGS. 3A and 3B, is a series of images demonstrating cytolytic activity of anti-mesothelin lentiviral vector-engineered T cells. FIG. 3A is an image showing that P4 CAR T cells are degranulate and express T cell activation markers in response to mesothelin-specific stimulation. P4 CAR T cells were cultured without target cells (none) or with the indicated mesothelin-negative or positive tumor cell targets for 5 hours while being stained by an anti-CD107 antibody conjugated with FITC. After the incubation period, T cells were stained for CD8 and CD69 and analyzed by flow cytometry. FIG. 3B is an image showing antigen-specific killing of mesothelin$^+$ tumor cells by P4 CAR T cells. Primary human T cells transduced to express either P4-z or anti-CD19-z CARs or GFP were co-cultured with Cr$^{51}$-labeled native AE17, AE17M, A1847 and C30 cell lines for 4 hrs at the indicated effector to target ratio. Percent specific target cell lysis was calculated as (experimental−spontaneous release)÷(maximal−spontaneous release)×100. Error bars indicate standard deviation.

FIG. 4, comprising FIG. 4A is an image of mesothelin immunostaining showing regional diversity of mesothelin expression in high-grade papillary serous ovarian adenocarcinoma. Original magnification was 200×. FIG. 4B is a heatmap illustration of mesothelin expression level in primary and metastatic ovarian carcinoma cases. FIG. 4C is an image demonstrating that P4-z CAR T cells were co-cultured with antigen-negative Cr$^{51}$-labeled AE17 (upper) or C30 tumor cells (lower) in the presence or absence of unlabelled antigen-positive AE17M (upper) or A1847 cells (lower), respectively, for 4 hrs (left panels) and 18 hrs (right panels) at the indicated effector to target ratio. As positive controls, P4-z CAR T cells were co-cultured with antigen-positive $Cr^{51}$-labeled AE17M (upper) or A1847 tumor cells (lower) in the presence or absence of unlabelled antigen-negative AE17 (upper) or C30 cancer cells (lower), respectively. Percent specific target cell lysis was calculated as (experimental−spontaneous release)÷(maximal−spontaneous release)×100. Error bars indicate standard deviation.

FIG. 5, comprising FIG. 5A is an image demonstrating that soluble mesothelin is present in the supernatant of mesothelin expressing tumor cells and in the ovarian cancer-derived ascites fluid. Tumor-free cell supernatants or ascites fluid were analyzed for the presence of soluble mesothelin using an ELISA assay. FIG. 5B, is an image demonstrating that anti-mesothelin T cells were incubated with mesothelin+ tumor cells in the presence of A1847 mesothelin rich medium or RPMI 10% FBS medium. After overnight incubation, supernatants were assayed for IFN-γ by ELISA. Results depict the mean±SEM of triplicate wells. FIG. 5C, is an image demonstrating that T cells were incubated overnight with AE17M and A1847 tumor cells in the presence or absence of soluble mesothelin or control. The amount of IFN-γ in culture supernatants was determined using ELISA (results depict the mean±SEM of triplicate wells). FIG. 5D, is an image demonstrating results from a mesothelin dissociation assay. P4-z CAR T cells were labeled with recombinant biotinylated mesothelin and then incubated at 37° C. or 4° C. in a time course in the presence of a 10-fold excess of non-biotinylated mesothelin. Antigen retention on the cell surface was assessed by flow cytometry by adding SA-PE after the end of each culture period. (Upper) Percent retained mesothelin (y-axis) was normalized and scored as mean fluorescence intensity (MFI) post-incubation÷pre-incubation MFI×100. (Lower) The percentage of pre-bound CD3+ T cells with positive mesothelin binding compared to similarly treated untransduced T cells from the same donor as control was plotted on the y-axis.

FIG. 6, comprising FIGS. 6A through 6F, is a series of images demonstrating that mesothelin re-directed T cells exert potent effector functions in vivo. FIG. 6A is an image demonstrating rapid regression of large pre-established tumors in vivo by P4-28z CART cells: effect of the CD28 costimulatory signaling domain. NSG mice bearing established s.c. tumor were treated with i.t. injections of 5×10$^6$ P4-z and P4-28z CAR+ T cells or control anti-CD19-28z and GFP T cells or saline on day 45 and 55. Tumor growth was assessed by caliper measurement. Tumors treated with P4-28z CAR-transduced T cells (~75% CAR expression) rapidly regressed (arrows indicate days of T cell infusion); tumors treated with saline, GFP or CD19-28z CAR transduced T cells did not regress 3 weeks post-first T cell dose (p<0.05). Equal doses of P4-z CAR-transduced T cells (~75% CAR expression) only slowed the tumor growth (p=0.05). Results are expressed as a mean tumor volume (mm$^3$±SEM) with n=5 for all groups. FIG. 6B is an image demonstrating that A1847 fLuc+ bioluminescence signal was decreased in P4-z and P4-28z CAR treated mice compared with the anti-CD19-28z and the control treatment groups 3 weeks after the first T cell dose. FIG. 6C is an image demonstrating that P4-28z T cells inhibit tumor outgrowth and ascites formation in A1847 murine model of peritoneal carcinomatosis. NSG mice received i.p. injection of 10×10$^6$ A1847 fLuc+ tumor cells and were randomized into two groups before beginning therapy with 10×10$^6$ T cells expressing P4-28z or CD19-28z via i.v. infusion on day 14 and 19 after tumor inoculation. Tumor growth was monitored by bioluminescence imaging (days 12 and 29 shown). Photon emission from fLuc+ tumor cells was quantified and the mean±SEM bioluminescence signal determined with n=5 for both groups. FIG. 6D is an image demonstrating that A1847 fLuc+ bioluminescence signal was rapidly decreased and reached the background luminescence level in P4-28z CAR treated mice compared with the anti-CD19-28z 2 weeks after the first T cell dose. FIG. 7E is an image demonstrating that stable persistence of P4 CAR engineered human T cells in vivo. Peripheral blood was collected 3 weeks after the first T cell infusion and quantified for the absolute number of human CD4+ and CD8+ T cells/ul of blood. Mean cell count±SEM is shown with n=5 for all groups. FIG. 6F is an image demonstrating that surface CAR expression on persisting P4+ and anti-CD19-specific human CD3+ T cells derived from the blood of treated mice measured by flow cytometry. Mean CAR+ expression frequency per CD3+ T cell±SEM per group is shown with n=5 for all groups.

FIG. 9, comprising FIG. 9A is an image showing the frequency of all sites expressing mesothelin at levels ranging from 0 to 3. FIG. 9B, is an image showing the frequency of either primary or metastatic all sites expressing mesothelin at levels ranging from 0 to 3.

FIG. 10, comprising FIG. 10A is an image demonstrating that tumor-secreted mesothelin does not bind to mesothelin-negative tumor cells. Mesothelin protein binding (solid black histograms) to antigen-negative C30 tumor cells incubated with either supernatant derived from the same line (C30) or from A1847 was evaluated by flow cytometry. The native C30 cell line which does not express human mesothelin (open gray histogram) was engineered to express high surface levels of human mesothelin (C30M) as shown by flow cytometry (solid black histogram) and served as the positive control for the staining. FIG. 10B is an image demonstrating that tumor secreted mesothelin does not render mesothelin-negative tumors susceptible to P4 T cell recognition and cytokine secretion. P4-28z and anti-CD19-28z (10$^5$ CAR+ T cells) were cultured alone (none) or stimulated overnight with an equal number of human C30 tumor cells in the presence or absence of tumor released-mesothelin, C30M or A1847 tumor cells. Mean IFN-γ concentration±SEM (pg/ml)

from triplicate cultures is shown. FIG. 10C is an image demonstrating that tumor secreted mesothelin does not render mesothelin-negative tumors susceptible to P4 CART cell-mediated cytotoxicity. P4-28z or anti-CD19-28z CARs T cells were co-cultured with either $Cr^{51}$-labeled C30 tumor cells in the presence or absence of tumor released-mesothelin or C30M at the indicated effector to target cell ratio. Percent specific target cell lysis was calculated as (experimental−spontaneous release)÷(maximal−spontaneous release)×100. Bars indicate standard deviation. Shown is the 4 hr time point.

FIG. 11, comprising FIGS. 11A through 11D, is a series of images depicting in vitro cytokine secretion and in vivo persistence of first and second generation P4 CAR T cells. FIG. 11A is an image depicting enhanced antigen-specific IFN-γ secretion by P4-28z compared with P4-z CAR T cells following overnight incubation with cancer cell lines expressing or not mesothelin. Mean IFN-γ concentration±SEM (pg/ml) from duplicate cultures is shown. FIG. 11B is an image depicting superior production of Th1 cytokines (IL-2 and TNF-a) by primary human P4-28z T cells compared with P4-z CAR T cells upon co-culture with mesothelin-expressing A1847 tumor cells. Cell-free supernatant from three independent cultures was harvested and pooled after overnight incubation and the indicated human Th1/Th2 cytokines were quantified using cytometric bead array technology. Values represent cytokine concentration (pg/ml). FIG. 11C is an image showing that peripheral blood was collected 2 weeks after the last T cell infusion and quantified for the absolute number of human $CD4^+$ and $CD8^+$ T cells/μl of blood. Mean cell count±SEM per group is shown with n=5 for all groups. FIG. 11D is an image showing surface CAR expression on persisting $P4^+$ and anti-CD19-specific human $CD3^+$ T cells derived from the blood of treated mice measured by flow cytometry. Mean $CAR^+$ expression frequency per $CD3^+$ T cell±SEM per group is shown with n=5 for all groups.

DETAILED DESCRIPTION

Figure 1A:
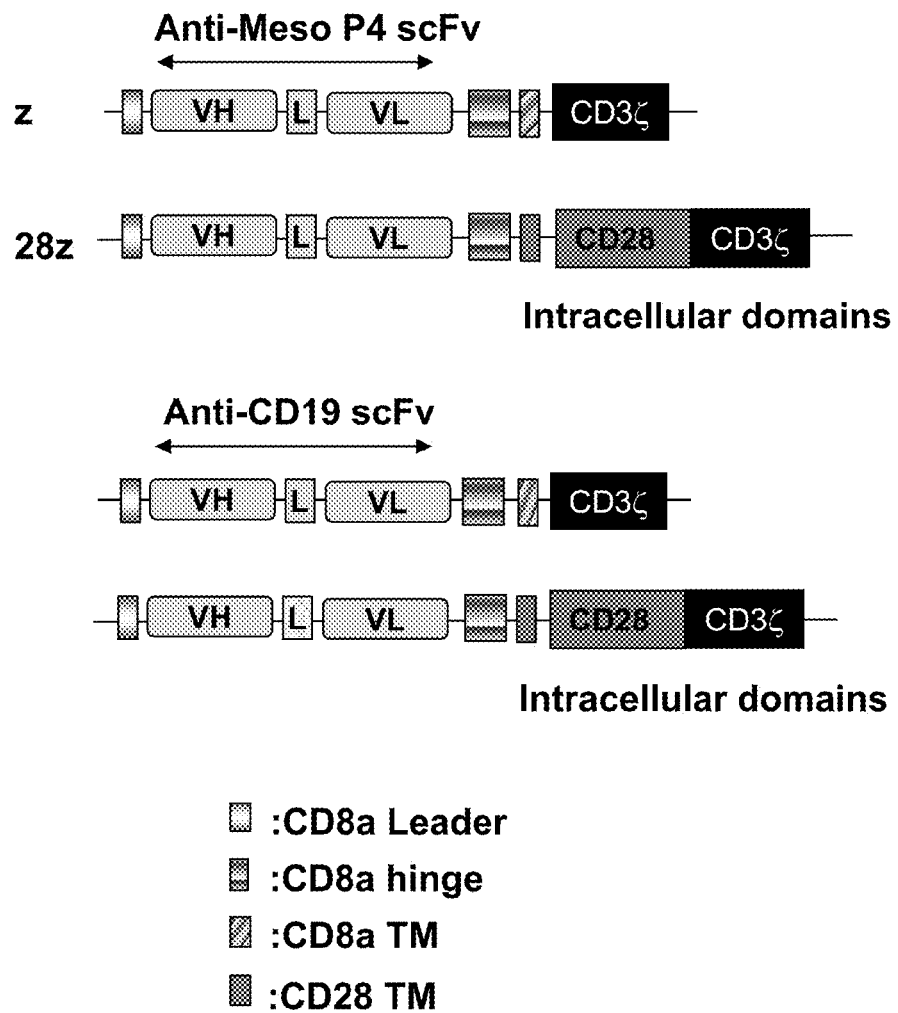
FIGS. 1A and 1B, is a series of images depicting the generation and specific immune recognition by P4 anti-mesothelin CAR-transduced human T cells in vitro.

The present invention relates generally to the treatment of a patient having a cancer associated with dysregulated expression of mesothelin, or at risk of having a cancer associated with dysregulated expression of mesothelin, using lymphocyte infusion. Preferably, autologous lymphocyte infusion is used in the treatment. In one embodiment, autologous PBMCs are collected from a patient in need of treatment and T cells therefrom are engineered and expanded using the methods described herein and then infused back into the patient.

The present invention relates generally to the use of T cells engineered to express a Chimeric Antigen Receptor (CAR). CARS combine an antigen recognition domain of a specific antibody with an intracellular signaling molecule. For example, the intracellular signaling molecule can include but is not limited to CD3-zeta chain, 4-1BB and CD28 signaling modules and combinations thereof. Preferably, the antigen recognition domain binds to mesothelin. More preferably, the antigen recognition domain comprises a fully human anti-mesothelin. Accordingly, the invention provides a fully human anti-mesothelin-CAR engineered into a T cell and methods of their use for adoptive therapy.

In one embodiment, the invention includes autologous cells that are transfected with a vector comprising a fully-human anti-mesothelin CAR transgene. Preferably, the vector is a retroviral vector. More preferably, the vector is a self-inactivating lentiviral vector as described elsewhere herein.

In one embodiment, the anti-mesothelin-CAR T cells of the invention can be generated by introducing a lentiviral vector comprising a mesothelin binding domain, CD8α hinge and transmembrane domain, and a CD3zeta signaling domain into the cells. In some instances, the vector further comprises the signaling domain of 4-1BB, CD28, or a combination of both. In one embodiment, the CAR-modified T cells of the invention are able to replicate in vivo resulting in long-term persistence that can lead to sustained tumor control.

DEFINITIONS

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "autoimmune disease" as used herein is defined as a disorder that results from an autoimmune response. An autoimmune disease is the result of an inappropriate and excessive response to a self-antigen. Examples of autoimmune diseases include but are not limited to, Addision's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

The term "dysregulated" when used in the context of the level of expression or activity of mesothelin refers to the level of expression or activity that is different from the expression level or activity of mesothelin in an otherwise identical healthy animal, organism, tissue, cell or component thereof. The term "dysregulated" also refers to the altered regulation of the level of expression and activity of mesothelin compared to the regulation in an otherwise identical healthy animal, organism, tissue, cell or component thereof.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fe), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

As used herein "mesothelin" refers to a differentiation antigen whose expression in normal human tissues is limited to mesothelial cells lining the pleura, pericardium and peritoneum. However, mesothelin is highly expressed in several human cancers, including mesotheliomas, pancreatic adenocarcinomas, ovarian cancers and lung adenocarcinomas. The mesothelin gene encodes a precursor protein of 71 kDa that is processed to a 31 kDa shed protein called megakaryocyte potentiating factor (MPF) and a 40 kDa fragment, mesothelin, that is attached to the cell membrane by a glycosylphosphatidylinositol (GPI) anchor. The term "mesothelin" includes variants, isoforms, homologs, orthologs and paralogs. For example, antibodies specific for a human mesothelin protein may, in certain cases, cross-react with a mesothelin protein from a species other than human. In other embodiments, the antibodies can be completely specific for the human mesothelin protein and not exhibit species or other types of cross-reactivity, or cross-react with mesothelin from certain other species but not all other species (e.g., cross-react with a primate mesothelin but not mouse mesothelin).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell. An example of a "cell surface receptor" is human mesothelin.

"Single chain antibodies" refer to antibodies formed by recombinant DNA techniques in which immunoglobulin heavy and light chain fragments are linked to the Fv region via an engineered span of amino acids. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334:54454; Skerra et al. (1988) Science 242:1038-1041.

The term "subject" is intended to include living organisms in which an immune response can be elicited (e.g., mammals).

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides compositions and methods for treating, among other diseases, cancer or any malignancy or autoimmune disease in which expression of mesothelin is dysregulated.

In one embodiment, the invention provides a cell (e.g., T cell) engineered to express a chimeric antigen receptor (CAR) wherein the CAR T cell exhibits an antitumor property. A preferred antigen is mesothelin. In one embodiment, the antigen recognition domain of the CAR comprises a fully human anti-mesothelin. Accordingly, the invention provides a fully human anti-mesothelin-CAR engineered into a T cell and methods of its use for adoptive therapy.

In one embodiment, the anti-mesothelin-CAR comprises one or more intracellular domain selected from the group of a CD137 (4-1BB) signaling domain, a CD28 signaling domain, a CD3zeta signal domain, and any combination thereof. This is because the present invention is partly based on the discovery that CAR-mediated T-cell responses can be further enhanced with the addition of costimulatory domains. For example, inclusion of the CD28 signaling domain significantly increased anti-tumor activity and in vivo persistence of CAR T cells compared to an otherwise identical CAR T cell not engineered to express CD28.

The present invention encompasses a cell (e.g., T cell) transduced with a lentiviral vector (LV). Moreover, the LV encodes a chimeric antigen receptor (CAR) which combines an antigen recognition domain of a specific antibody with an intracellular domain of CD3-zeta, CD28, 4-1BB, or any combinations thereof. Therefore, in some instances, the transduced T cell can elicit a CAR-mediated T-cell response.

Composition

The present invention encompasses a recombinant DNA construct comprising sequences of a fully human CAR, wherein the sequence comprises the nucleic acid sequence of a mesothelin binding domain operably linked to the nucleic acid sequence of an intracellular domain. The intracellular domain or otherwise the cytoplasmic domain comprises, a costimulatory signaling region and a zeta chain portion. The costimulatory signaling region refers to a portion of the CAR comprising the intracellular domain of a costimulatory molecule. Costimulatory molecules are cell surface molecules other than antigens receptors or their ligands that are required for an efficient response of lymphocytes to antigen.

Between the extracellular domain and the transmembrane domain of the CAR, or between the cytoplasmic domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Antigen Binding Moiety

In one embodiment, the CAR of the invention comprises a target-specific binding element otherwise referred to as an antigen binding moiety. The choice of moiety depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen moiety domain in the CAR of the invention include those associated with viral, bacterial and parasitic infections, autoimmune disease and cancer cells.

In one embodiment, the CAR of the invention can be engineered to target a tumor antigen of interest by way of engineering a desired antigen binding moiety that specifically binds to an antigen on a tumor cell. In the context of the present invention, "tumor antigen" or "hyperproliferative disorder antigen" or "antigen associated with a hyperproliferative disorder," refers to antigens that are common to specific hyperproliferative disorders such as cancer. The antigens discussed herein are merely included by way of example. The list is not intended to be exclusive and further examples will be readily apparent to those of skill in the art.

In a preferred embodiment, the antigen binding moiety portion of the CAR targets mesothelin, preferably human mesothelin.

The antigen binding domain can be any domain that binds to the antigen including but not limited to monoclonal antibodies, polyclonal antibodies, synthetic antibodies, human antibodies, humanized antibodies, and fragments thereof. In some instances, it is beneficial for the antigen binding domain to be derived from the same species in which the CAR will ultimately be used in. For example, for use in humans, it may be beneficial for the antigen binding domain of the CAR to comprise a human antibody or fragment thereof. Thus, in one embodiment, the antigen biding domain portion comprises a human antibody or a fragment thereof.

For in vivo use of antibodies in humans, it may be preferable to use human antibodies. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO98/16654, WO 96/34096, WO 96/33735, and WO 91/10741; each of which is incorporated herein by reference in its entirety. A human antibody can also be an antibody wherein the heavy and light chains are encoded by a nucleotide sequence derived from one or more sources of human DNA.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Anti-mesothelin antibodies directed against the human mesothelin antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (Int. Rev. Immunol., 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., Proc. Natl. Acad. Sci. USA, 90:2551 (1993); Jakobovits et al., Nature, 362:255-258 (1993); Bruggermann et al., Year in Immunol., 7:33 (1993); and Duchosal et al., Nature, 355:258 (1992).

Human antibodies can also be derived from phage-display libraries (Hoogenboom et al., J. Mol. Biol., 227:381 (1991); Marks et al., J. Mol. Biol., 222:581-597 (1991); Vaughan et al., Nature Biotech., 14:309 (1996)). Phage display technology (McCafferty et al., Nature, 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., J. Mol. Biol., 222:581-597 (1991), or Griffith et al., EMBO J., 12:725-734 (1993). See, also, U.S. Pat. Nos. 5,565,332 and 5,573,905, each of which is incorporated herein by reference in its entirety.

Human antibodies may also be generated by in vitro activated B cells (see, U.S. Pat. Nos. 5,567,610 and 5,229,275, each of which is incorporated herein by reference in its entirety). Human antibodies may also be generated in vitro using hybridoma techniques such as, but not limited to, that described by Roder et al. (Methods Enzymol., 121:140-167 (1986)).

Alternatively, in some embodiments, a non-human antibody is humanized, where specific sequences or regions of the antibody are modified to increase similarity to an antibody naturally produced in a human. In one embodiment, the antigen binding domain portion is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5): 489-498; Studnicka et al., 1994, Protein Engineering, 7(6): 805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. No. 6,407,213, U.S. Pat. No. 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239: 1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

In some instances, a human scFv may also be derived from a yeast display library.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

Antibodies can be humanized with retention of high affinity for the target antigen and other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A "humanized" antibody retains a similar antigenic specificity as the original antibody, i.e., in the present invention, the ability to bind human mesothelin. However, using certain methods of humanization, the affinity and/or specificity of binding of the antibody for human mesothelin may be increased using methods of "directed evolution," as described by Wu et al., J. Mol. Biol., 294:151 (1999), the contents of which are incorporated herein by reference herein in their entirety.

In one embodiment, the antigen binding moiety portion of the CAR of the invention targets mesothelin. Preferably, the antigen binding moiety portion in the CAR of the invention is a fully human anti-mesothelin scFV, wherein the nucleic acid sequence of the human anti-mesothelin scFV comprises the sequence set forth in SEQ ID NO: 12. In one embodiment, the human anti-mesothelin scFV comprises the nucleic acid sequence that encodes the amino acid sequence of SEQ ID NO: 11. In another embodiment, the human anti-mesothelin scFV portion of the CAR of the invention comprises the amino acid sequence set forth in SEQ ID NO: 11.

Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. In some instances, a variety of human hinges can be employed as well including the human Ig (immunoglobulin) hinge.

In one embodiment, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In one embodiment, the transmembrane domain in the CAR of the invention is the CD8 transmembrane domain. In one embodiment, the CD8 transmembrane domain comprises the nucleic acid sequence of SEQ ID NO: 18. In one embodiment, the CD8 transmembrane domain comprises the nucleic acid sequence that encodes the amino acid sequence of SEQ ID NO: 17. In another embodiment, the CD8 transmembrane domain comprises the amino acid sequence of SEQ ID NO: 17.

In one embodiment, the transmembrane domain in the CAR of the invention is the CD28 transmembrane domain. In one embodiment, the CD28 transmembrane domain comprises the nucleic acid sequence of SEQ ID NO: 16. In one embodiment, the CD28 transmembrane domain comprises the nucleic acid sequence that encodes the amino acid sequence of SEQ ID NO: 15. In another embodiment, the CD28 transmembrane domain comprises the amino acid sequence of SEQ ID NO: 15.

In some instances, the transmembrane domain of the CAR of the invention comprises the CD8a hinge domain. In one embodiment, the CD8a hinge domain comprises the nucleic acid sequence of SEQ ID NO: 14. In one embodiment, the CD8a hinge domain comprises the nucleic acid sequence that encodes the amino acid sequence of SEQ ID NO: 13. In another embodiment, the CD8a hinge domain comprises the amino acid sequence of SEQ ID NO: 13.

Cytoplasmic Domain

The cytoplasmic domain or otherwise the intracellular signaling domain of the CAR of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3-zeta.

In a preferred embodiment, the cytoplasmic domain of the CAR can be designed to comprise the CD3-zeta signaling domain by itself or combined with any other desired cytoplasmic domain(s) useful in the context of the CAR of the invention. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention in exemplified primarily with CD28 and 4-1BB as the co-stimulatory signaling element, other costimulatory elements are within the scope of the invention.

The cytoplasmic signaling sequences within the cytoplasmic signaling portion of the CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the cytoplasmic domain is designed to comprise the signaling domain of CD3-zeta and the signaling domain of CD28. In another embodiment, the cytoplasmic domain is designed to comprise the signaling domain of CD3-zeta and the signaling domain of 4-1BB.

In one embodiment, the cytoplasmic domain in the CAR of the invention is designed to comprise the signaling domain of CD28 and the signaling domain of CD3-zeta, wherein the signaling domain of CD28 comprises the nucleic acid sequence set forth in SEQ ID NO: 22 and the signaling domain of CD3-zeta comprises the nucleic acid sequence set forth in SEQ ID NO: 24. In another embodiment, the signaling domain of CD28 comprises the amino acid sequence of SEQ ID NO: 21 and the signaling domain of CD3-zeta comprises the amino acid sequence of SEQ ID NO: 23.

In one embodiment, the cytoplasmic domain in the CAR of the invention is designed to comprise the signaling domain of 4-1BB and the signaling domain of CD3-zeta, wherein the signaling domain of 4-1BB comprises the nucleic acid sequence set forth in SEQ ID NO: 20 and the signaling domain of CD3-zeta comprises the nucleic acid sequence set forth in SEQ ID NO: 24. In another embodiment, the signaling domain of 4-1BB comprises the amino acid sequence of SEQ ID NO: 19 and the signaling domain of CD3-zeta comprises the amino acid sequence of SEQ ID NO: 23.

Vectors

The present invention encompasses a DNA construct comprising sequences of a CAR, wherein the sequence comprises the nucleic acid sequence of an antigen binding moiety operably linked to the nucleic acid sequence of an intracellular domain. An exemplary intracellular domain that can be used in the CAR of the invention includes but is not limited to the intracellular domain of CD3-zeta, CD28, 4-1BB, and the like. In some instances, the CAR can comprise any combination of CD3-zeta, CD28, 4-1BB, and the like.

In one embodiment, the CAR of the invention comprises an anti-mesothelin (e.g., P4 scFv), CD8a hinge domain, CD28 transmembrane, and CD28 and CD3zeta signaling domains. In another embodiment, the CAR of the invention comprises an anti-mesothelin (e.g., P4 scFv), CD8a hinge domain, CD8 transmembrane, and 4-1BB and CD3zeta signaling domains.

In one embodiment, the CAR of the invention comprises the nucleic acid sequence set forth in SEQ ID NO: 4. In another embodiment, the CAR of the invention comprises the nucleic acid sequence set forth in SEQ ID NO: 6. In a further embodiment, the CAR of the invention comprises the nucleic acid sequence set forth in SEQ ID NO: 8.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onto-retroviruses such as murine leukemia viruses in that they can transduce non-proliferating cells, such as hepatocytes. They also have the added advantage of low immunogenicity.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., MOLECULAR CLONING: A LABORATORY MANUAL, volumes 1-3 ($3^{rd}$ ed., Cold Spring Harbor Press, NY 2001), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., MOLECULAR CLONING: A LABORATORY MANUAL volumes 1-3 ($3^{rd}$ ed., Cold Spring Harbor Press, NY 2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Genetically Modified T Cells

In some embodiments, the CAR sequences are delivered into cells using a retroviral or lentiviral vector. CAR-expressing retroviral and lentiviral vectors can be delivered into different types of eukaryotic cells as well as into tissues and whole organisms using transduced cells as carriers or cell-free local or systemic delivery of encapsulated, bound or naked vectors. The method used can be for any purpose where stable expression is required or sufficient.

In other embodiments, the CAR sequences are delivered into cells using in vitro transcribed mRNA. In vitro transcribed mRNA CAR can be delivered into different types of eukaryotic cells as well as into tissues and whole organisms using transfected cells as carriers or cell-free local or systemic delivery of encapsulated, bound or naked mRNA. The method used can be for any purpose where transient expression is required or sufficient.

In another embodiment, the desired CAR can be expressed in the cells by way of transponsons.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the chimeric receptor mRNAs with different structures and combination of their domains. For example, varying of different intracellular effector/costimulator domains on multiple chimeric receptors in the same cell allows determination of the structure of the receptor combinations which assess the highest level of cytotoxicity against multi-antigenic targets, and at the same time lowest cytotoxicity toward normal cells.

One advantage of RNA transfection methods of the invention is that RNA transfection is essentially transient and a vector-free: an RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. Preferably, it is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct can be delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. No. 6,678,556, U.S. Pat. No. 7,171,264, and U.S. Pat. No. 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. No. 6,567,694; U.S. Pat. No. 6,516,223, U.S. Pat. No. 5,993,434, U.S. Pat. No. 6,181,964, U.S. Pat. No. 6,241,701, and U.S. Pat. No. 6,233, 482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Sources of T Cells

Prior to expansion and genetic modification, a source of T cells is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or, lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5 \times 10^6$/ml. In other embodiments, the concentration used can be from about $1 \times 10^5$/ml to $1 \times 10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

T cells are activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4$^+$ T cells or CD8$^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., *Transplant Proc.* 30(8): 3975-3977, 1998; Haanen et al., *J. Exp. Med.* 190(9):13191328, 1999; Garland et al., *J. Immunol Meth.* 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for CD4$^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle:cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4+) that is greater than the cytotoxic or suppressor T cell population ($T_C$, CD8+). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

In one embodiment, the invention pertains to a method of inhibiting growth of a mesothelin-expressing tumor cell, comprising contacting the tumor cell with the fully human anti-mesothelin CART cell of the present invention, such that growth of the tumor cell is inhibited. Preferably, the mesothelin-expressing tumor cell is a mesothelioma cell, pancreatic tumor cell, ovarian tumor cell, stomach tumor cell, lung tumor cell or endometrial tumor cell. In other embodiments, the mesothelin-expressing tumor cell is from a cancer selected from the group consisting of mesothelioma, papillary serous ovarian adenocarcinoma, clear cell ovarian carcinoma, mixed Mullerian ovarian carcinoma, endometroid mucinous ovarian carcinoma, pancreatic adenocarcinoma, ductal pancreatic adenocarcinoma, uterine serous carcinoma, lung adenocarcinoma, extrahepatic bile duct carcinoma, gastric adenocarcinoma, esophageal adenocarcinoma, colorectal adenocarcinoma and breast adenocarcinoma.

In another aspect, the invention pertains to a method of treating cancer in a subject. The method comprises administering to the subject a fully human anti-mesothelin CAR T cell of the present invention such that the cancer is treated in the subject. Particularly preferred cancers for treatment are mesotheliomas, pancreatic cancers, ovarian cancers, stomach cancers, lung cancers and endometrial cancers. In still other embodiments, the cancer to be treated is selected from the group consisting of mesotheliomas, papillary serous ovarian adenocarcinomas, clear cell ovarian carcinomas, mixed Mullerian ovarian carcinomas, endometroid mucinous ovarian carcinomas, pancreatic adenocarcinomas, ductal pancreatic adenocarcinomas, uterine serous carcinomas, lung adenocarcinomas, extrahepatic bile duct carcinomas, gastric adenocarcinomas, esophageal adenocarcinomas, colorectal adenocarcinomas and breast adenocarcinomas.

The present invention includes a type of cellular therapy where T cells are genetically modified to express a chimeric antigen receptor (CAR) and the CAR T cell is infused to a recipient in need thereof. The infused cell is able to kill tumor cells in the recipient. Unlike antibody therapies, CAR-modified T cells are able to replicate in vivo resulting in long-term persistence that can lead to sustained tumor control. In various embodiments, the T cells administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T cell to the patient.

Without wishing to be bound by any particular theory, the anti-tumor immunity response elicited by the CAR-modified T cells may be an active or a passive immune response. In another embodiment, the fully-human CAR transduced T cells exhibit specific proinflammatory cytokine secretion and potent cytolytic activity in response to human cancer cells expressing the mesothelin, resist soluble mesothelin inhibition, mediate bystander killing and mediate regression of an established human tumor. For example, antigen-less tumor cells within a heterogeneous field of mesothelin-expressing tumor may be susceptible to indirect destruction by mesothelin-redirected T cells that has previously reacted against adjacent antigen-positive cancer cells.

The fully-human CAR-modified T cells of the invention may be a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding a CAR to the cells or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified T cells of the invention are used in the treatment of diseases, disorders and conditions associated with dysregulated expression of mesothelin. In certain embodiments, the cells of the invention are used in the treatment of patients at risk for developing diseases, disorders and conditions associated with dysregulated expression of mesothelin. Thus, the present invention provides methods for the treatment or prevention of diseases, disorders and conditions associated with dysregulated expression of mesothelin comprising administering to a subject in need thereof, a therapeutically effective amount of the fully human CAR-modified T cells of the invention.

The CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol, may select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Redirected Anti-Tumor Activity of Primary Human Lymphocytes Transduced with a Fully-Human Anti-Mesothelin Chimeric Receptor Cancer regression by gene-modified T cells bearing a chimeric antigen receptor (CAR) exodomain of mouse origin can be limited by the induction of transgene immunogenicity resulting in poor persistence and function in vivo. The development of functionally-active CAR of human origin can address this issue. The results presented herein demonstrate the constructing and evaluation of a fully-human anti-mesothelin CAR comprising a human mesothelin-specific single-chain antibody variable fragment (P4 scFv) coupled to T cell signaling domains. Briefly, it was observed that primary human T cells expressing P4 CAR specifically produced proinflammatory cytokines, degranulated and exerted potent cytolytic functions when cultured with mesothelin-expressing tumors in vitro. P4 CAR T cells also mediated bystander killing of mesothelin-negative cancer cells during co-culture. CAR reactivity was not abrogated by soluble tumor-secreted or recombinant mesothelin protein even at supraphysiological levels. Importantly, adoptive transfer of P4 CAR-expressing T cells mediated the regression of large, established tumor in the presence of soluble mesothelin in a xenogenic model of human ovarian cancer. Thus, primary human T cells expressing fully-human anti-mesothelin CAR efficiently killed mesothelin-expressing tumors in vitro and in vivo.

The materials and methods employed in these experiments are now described.

Materials and Methods

Anti-Mesothelin CAR Construction

The pTOR002 plasmid containing the anti-mesothelin scFv P4 (Bergan, et al., 2007, Cancer Lett 255: 263-274; Scholler, et al., 2006, J Immunol Methods 317: 132-143) was used as a template for PCR amplification of a 795-bp P4 fragment using the following primers: 5'-GCGAGATCT-CAGGTACAGCTGCAGCAGTC-3'; SEQ ID NO: 1, (BglII is underlined) and 5'-CGCGCTAGCGGAGAGGACGGT-CAGTTGGG-3'; SEQ ID NO: 2, (NheI is underlined). The resulting PCR product containing a BglII site on the 5'-end and a NheI site on the 3'-end was digested with the relevant enzymes. Third generation self-inactivating lentiviral expression vectors pELNS were digested with BamHI and NheI to create compatible cohesive ends and gel purified. The digested PCR products were then into the pELNS vector containing CD3z or CD28-CD3z T cell signalling domains in which transgene expression is driven by the EF-1α promoter. The resulting construct was designated pELNS-P4-z/CD28-z.

Recombinant Lentivirus Production

High-titer replication-defective lentiviral vectors were produced and concentrated as previously described. 293T human embryonic kidney cells were seeded at $10\times10^6$ per T-150 tissue culture flask 24 h before transfection. All plasmid DNA were purified using the QIAGEN Endo-free Maxi prep kit. Cells were transfected with 7 μg pVSV-G (VSV glycoprotein expression plasmid), 18 μg of ug pRSV.REV (Rev expression plasmid), 18 μg of pMDLg/p.RRE (Gag/Pol expression plasmid), and 15 μg of pELNS transfer plasmid using Express Inn (Open Biosytems). The viral supernatant was harvested at 24 and 48 h post-transfection. Viral particles were concentrated and resuspended in 0.4 ml by ultracentrifugation for 3 h at 25,000 rpm with a Beckman SW28 rotor (Beckman Coulter, Fullerton, Calif.).

Human T Cell Transduction

Primary human T cells, which were purchased from the Human Immunology Core at University of Pennsylvania, were isolated from healthy volunteer donors following leukapheresis by negative selection. All specimens were collected under a University Institutional Review Board-approved protocol, and written informed consent was obtained from each donor. T cells were cultured in complete media (RPMI 1640 supplemented with 10% heat inactivated fetal bovine serum (FBS), 100 U/ml penicillin, 100 μg/ml streptomycin sulfate, 10-mM HEPES), and stimulated with anti-CD3 and anti-CD28 mAbs coated beads (Invitrogen) as described (Levine, et al., 1997, J Immunol 159: 5921-5930). 12-24 hr after activation, T cells were transduced with lentiviral vectors at MOI of ~5-10. $CD4^+$ and $CD8^+$ T cells used for in vivo experiments were mixed at 1:1 ratio, activated, and transduced. Human recombinant interleukin-2 (Novartis) was added every other day to a 50 IU/ml final concentration. Cell density of $0.5-1\times10^6$ cells/ml was maintained. Rested engineered T cells were adjusted for identical transgene expression prior to functional assays.

Cell Lines

Lentivirus packaging was performed in the immortalized normal fetal renal 293T cell line purchased from ATCC. Human cell lines used in immune based assays include the established human ovarian cancer cell lines SKOV3, A1847, OVCAR3, OVCAR5, OVCAR-2, and C30. For bioluminescence assays, target cancer cell lines were transfected to express firefly luciferase (fLuc), enriched by antibiotic selection positive expression by bioluminescence imaging. For specificity controls, the mouse malignant mesothelioma cell line, AE17, was transduced with lentivirus to express human mesothelin (AE17-M). K562, a human erythroleukemic cell line, CD19-expressing K562 ($CD19^+K562$) cells, and mesothelin/CD19-expressing K562 ($Meso^+CD19^+K562$) cells were obtained. 293T cells and tumor cell lines were maintained in RPMI-1640 (Invitrogen) supplemented with 10% (v/v) heat-inactivated FBS, 2 mM L-glutamine, and 100 μg/mL penicillin and 100 U/mL streptomycin. All cell lines were routinely tested for mycoplasma contamination.

Cytokine Release Assays

Cytokine release assays were performed by coculture of $1\times10^5$ T cells with either soluble or immobilized yeast-derived recombinant mesothelin or $1\times10^5$ target cells per well in triplicate in 96-well round bottom plates in a final volume of 200 ul of T cell media. After 20~24 hr, co-culture supernatants were assayed for presence of IFN-γ using an ELISA Kit, according to manufacturer's instructions (Biolegend). Values represent the mean of triplicate wells. IL-2, IL-4, IL-10, TNF-α and MIP-1α cytokines were measured by flow cytometry using Cytokine Bead Array, according to manufacturer's instructions (BD Biosciences).

Cytotoxicity Assays $^{51}Cr$ release assays were performed as described (Johnson, et al., 2006, J Immunol 177: 6548-6559). Target cells were labeled with 100 uCi $^{51}Cr$ at 37° C. for 1.5 hours. Target cells were washed three times in PBS, resuspended in CM at $10^5$ viable cells/mL, and 100 uL added per well of a 96-well V-bottom plate. Effector cells were washed twice in CM and added to wells at the given ratios. Plates were quickly centrifuged to settle cells, and incubated at 37° C. in a 5% $CO_2$ incubator for 4 or 18 hours after which time the supernatants were harvested, transferred to a lumar-plate (Packard) and counted using a 1450 Microbeta Liquid Scintillation Counter (Perkin-Elmer). For the bystander cytotoxicity assays, $^{51}Cr$ labeled mesothelin-negative target cells were mixed with unlabelled mesothelin-positive targets cells at a ratio 1:1 for a final concentration of $10^5$ viable cells/ml before being incubated with the effector T cells at the given ratios. Spontaneous $^{51}Cr$ release was evaluated in target cells incubated with medium alone. Maximal $^{51}Cr$ release was measured in target cells incubated with SDS at a final concentration of 2% (v/v). Percent specific lysis was calculated as (experimental−spontaneous lysis/maximal−spontaneous lysis) times 100.

Measurement of Soluble Secreted Mesothelin

Cell culture supernatants, ascites fluids and NOG mice derived serum were analysed for their mesothelin concentration using the Human Mesothelin DuoSet Kit (R&D Systems) according to the manufactures instructions.

Blocking Assays

Mesothelin positive A1847 tumor cells were seeded at wells of a 96-well U-bottom plate at $2\times10^5$ cell/200 ul and cultured overnight. The next day the media was removed and cells were washed once with PBS or left untreated. P4 CAR T cell were then added to the tumor cells left untreated or to whom fresh medium was added and the percentage of inhibition of tumor recognition was calculated. To calculate the background inhibition possibly derived from immunoinhibitory cytokines anti-CD19BBZ T cells were resuspended in either A1847 conditioned media prior their addition to adhered and washed K562-CD19 cells. For the blocking experiment using recombinant mesothelin P4 CARs were incubated with the A1847 or AE17M cells in the presence of 5 ug/ml recombinant mesothelin and the INF-γ secretion was determined after an overnight co-culture.

Immunohistochemistry

Institutional review board approval was obtained. Records from 18 consecutive patients with metastatic papillary serous ovarian cancer (FIGO stage IIB and above) undergoing primary resection at the institution between 2005 and 2008 were retrieved. Slides were reviewed and annotated and paraffin-embedded tissue blocks were selected to construct a tissue microarray of primary and metastatic tumors. Including primary sites and metastases, a total of 72 tumor deposits were represented on the array. A mean of 3.7 sites were included per patient. The most common metastatic sites included omentum, peritoneum (e.g., cul-de-sac), uterine serosa, and bowel wall. For each block, triplicate 0.6 mm cores of tumor were placed on a tissue microarray. Paraffin sections of the array (5 µm) were stained with anti-mesothelin (1:10, cat #MS-1320; NeoMarkers, Fremont, Calif.) according to standard protocols in the laboratory. Mesothelin expression in each core was scored by light microscopy at 200× magnification using a semiquantitative scale ranging from 0 to 3.

Antigen Dissociation Assay

P4 CAR or untransduced T cell were harvested, washed once with FACS buffer and stained with 0.5 ug/ml yeast-derived biotinylated mesothelin protein (Bergan, et al., 2007, Cancer Lett 255: 263-274) for 30 min at 4° C. Then the cells were washed two times before the addition of 5 µg/ml of non-biotinylated mesothelin competitor and incubation at a 4° C. or 37° C. for different time points (0<t>6 h). At indicated time points cells were removed from 4° C. or 37° C., washed again, labeled with biotinylated streptavidin, washed and analyzed for percent mesothelin-positive and mean fluorescence intensity by flow cytometry.

Xenograft Model of Ovarian Cancer

All animals were obtained from the Stem Cell and Xenograft Core of the Abramson Cancer Center, University of Pennsylvania. Six to 12-week-old NOD/SCID/γ-chain−/− (NSG) mice were bred, treated and maintained under pathogen-free conditions in-house under University of Pennsylvania IACUC approved protocols. For an established ovarian cancer model, 6 to 12-week-old female NSG mice were inoculated s.c. with $1 \times 10^6$ A1847 fLuc$^+$ cells on the flank on day 0. After tumors become palpable at about 6 weeks, human primary T cells were activated, and transduced as described elsewhere herein. After 2 weeks T cell expansion, when the tumor burden was ~150-250 mm$^3$, mice were injected intratumorally with T cells. Tumor dimensions were measured with calipers, and tumor volumes calculated using the formula $V = \frac{1}{2}(\text{length} \times \text{width}^2)$, where length is greatest longitudinal diameter and width is greatest transverse diameter. Animals were imaged prior to T cell transfer and about every week thereafter to evaluate tumor growth. Photon emission from fLuc$^+$ cells was quantified using the "Living Image" software (Xenogen) for all in vivo experiments. For the intraperitoneal model of ovarian cancer, 8 to 12-week-old NSG mice were injected i.p. with $10 \times 10^6$ A1847 fLuc$^+$ cells. Two weeks after peritoneal inoculation, mice bearing established A1847 tumors received i.v. administered T cells. Mice were sacrificed when they became distressed and moribund. To monitor the extent of tumor progression, the mice were imaged weekly. In all models, 5 mice were randomized per group prior to treatment.

Bioluminescence Imaging

Tumor growth was also monitored by Bioluminescent imaging (BLI). BLI was performed using Xenogen IVIS imaging system and the photons emitted from fLuc-expressing cells within the animal body were quantified using Living Image software (Xenogen). Briefly, mice bearing A1847 fLuc$^+$ tumor cells were injected intraperitoneally with D-luciferin (150 mg/kg stock, 100 µL of D-luciferin per 10 grams of mouse body weight) suspended in PBS and imaged under isoflurane anesthesia after 5~10 minutes. A pseudocolor image representing light intensity (blue, least intense; red, most intense) was generated using Living Image. BLI findings were confirmed at necropsy.

Flow Cytometric Analysis

The following MAbs were used for phenotypic analysis: PE mouse anti-Human CD3; FITC anti-human CD4; APC anti-human CD8; PE-anti-human CD45, APC-Cy7 anti-human CD69, FITC anti-human CD107a and FITC anti-human CD107b. 7-AAD was used for viability staining. All mAbs were purchased from BD Biosciences. In T cell transfer experiments, peripheral blood was obtained via retro-orbital bleeding and stained for the presence of human CD45, CD4, and CD8 T cells. After gating on the human CD45$^+$ population, the CD4$^+$ and CD8$^+$ subsets were quantified using Tru-Count tubes (BD Biosciences) with known numbers of fluorescent beads as described in the manufacturer's instructions. Tumor cell surface expression of mesothelin was performed using soluble P4 anti-mesothelin scFv followed by PE-labeled streptavidin. T cell surface expression of the P4 or anti-CD19 CAR was evaluated using V5-tagged recombinant mesothelin followed by Alexa-647 conjugated anti-V5 tag or biotinylated streptavidin. Acquisition and analysis was performed using a BD FACS CANTO II with DIVA software.

Degranulation Assay

The degranulation assay was performed as earlier described (Betts, et al., 2003, J Immunol Methods 281: 65-78) with minor modifications. Target cells ($1 \times 10^5$) were co-cultured with an equal number of effector cells in 0.1 mL per well in a 96-well plate in triplicate. Control wells contained either T cells alone. Anti-CD107a and Ab Anti-CD107b (10 ul per well) or IgG1 conjugated to FITC (BD Biosciences) were added in addition to 1 ul/sample of monensin (BD Biosciences) and incubated for 4-5 h at 37° C. Cells were washed 2 times with PBS, stained for expression of the P4 CAR, CD8 and CD69 and analyzed on a FACS DIVA II.

Statistical Analysis

Statistical analysis was performed using two-way repeated measures ANOVA for the tumor burden (tumor volume, photon counts). Student's t test was used to evaluate differences in absolute numbers of transferred T cells, cytokine secretion and specific cytolysis. Kaplan-Meier survival curves were compared using the log-rank test. GraphPad Prism 4.0 (GraphPad Software) was used for the statistical calculations. P<0.05 was considered significant.

The results of the experiments are now described.

CAR Construction

Figure 1B:
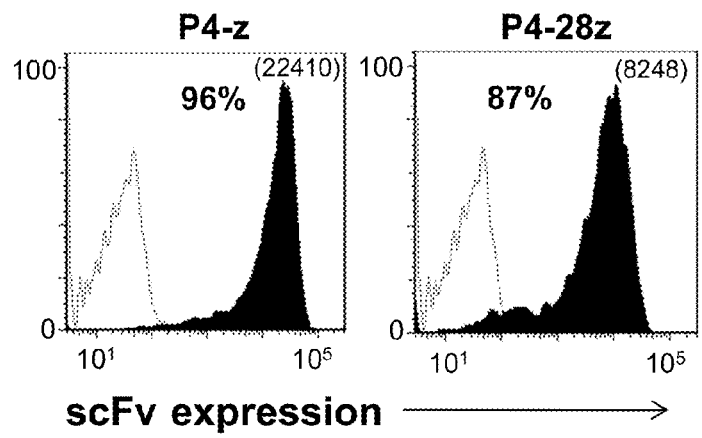
Figure 1B:
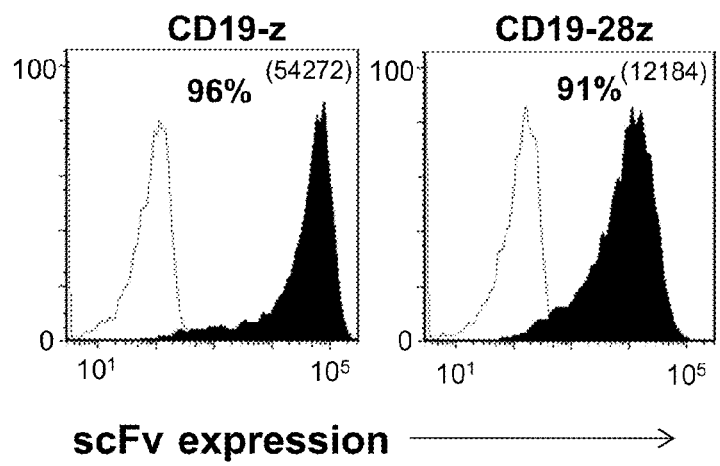

The human anti-human mesothelin-specific P4 scFv was selected for CAR construction based upon its high binding affinity and specificity for mesothelin ($10^8$-$10^9$ M$^{-1}$) (Bergan, et al., 2007, Cancer Lett 255: 263-274). P4 CAR constructs comprised the P4 scFv linked to a CD8a hinge and transmembrane region, followed by a CD3z signaling moiety alone (P4-z) or in tandem with the CD28 intracellular signaling motif were generated (P4-28z; FIG. 1A). An anti-CD19 CAR containing CD3z alone or with CD28 signaling motifs in tandem (CD19-28z) was used as an antigen specificity control (Milone, et al., 2009, Mol Ther 17: 1453-1464). Primary human T cells were efficiently transduced with CAR lentiviral vectors with transduction efficiencies reproducibly above 90% (FIG. 1B), and equilibrated to 80% by adding untransduced T cells for all functional assays. Sequences for CARs and components thereof are designated in Table 1.

TABLE 1

Sequence identifiers for CARs

| SEQ ID NO: # | IDENTITY |
|---|---|
| SEQ ID NO: 3 | P4-z (amino acid sequence) |
| SEQ ID NO: 4 | P4-z (nucleic acid sequence) |
| SEQ ID NO: 5 | P4-28z (amino acid sequence) |
| SEQ ID NO: 6 | P4-28z (nucleic acid sequence) |
| SEQ ID NO: 7 | P4-BBz (amino acid sequence) |
| SEQ ID NO: 8 | P4-BBz (nucleic acid sequence) |
| SEQ ID NO: 9 | CD8 Leader (amino acid sequence) |
| SEQ ID NO: 10 | CD8 Leader (nucleic acid sequence) |
| SEQ ID NO: 11 | P4 scFv (amino acid sequence) |
| SEQ ID NO: 12 | P4 scFv (nucleic acid sequence)t |
| SEQ ID NO: 13 | CD8a Hinge (amino acid sequence) |
| SEQ ID NO: 14 | CD8a Hinge (nucleic acid sequence) |
| SEQ ID NO: 15 | CD28 Transmembrane (amino acid sequence) |
| SEQ ID NO: 16 | CD28 Transmembrane (nucleic acid sequence) |
| SEQ ID NO: 17 | CD8 Transmembrane (amino acid sequence) |
| SEQ ID NO: 18 | CD8 Transmembrane (nucleic acid sequence) |
| SEQ ID NO: 19 | 4-1BB (amino acid sequence) |
| SEQ ID NO: 20 | 4-1BB (nucleic acid sequence) |
| SEQ ID NO: 21 | CD28 (amino acid sequence) |
| SEQ ID NO: 22 | CD28 (nucleic acid sequence) |
| SEQ ID NO: 23 | CD3 zeta (amino acid sequence) |
| SEQ ID NO: 24 | CD3 zeta (nucleic acid sequence) |

Primary Human P4 CAR T Cells Exert Antigen Specific Function In Vitro

Figure 2A:
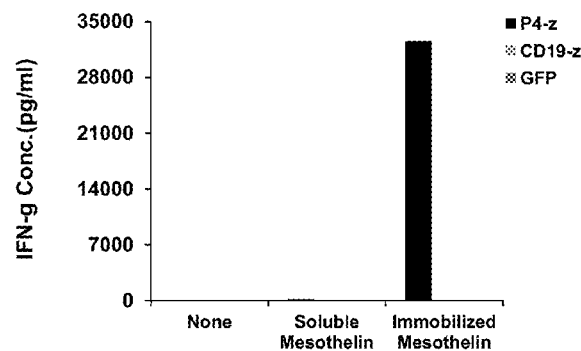
FIGS. 2A through 2E, is a series of images demonstrating that mesothelin re-directed T cells secrete Th1 proinflammatory cytokines in response to plate-bound mesothelin or tumor cell surface-associated mesothelin.
Figure 2B:
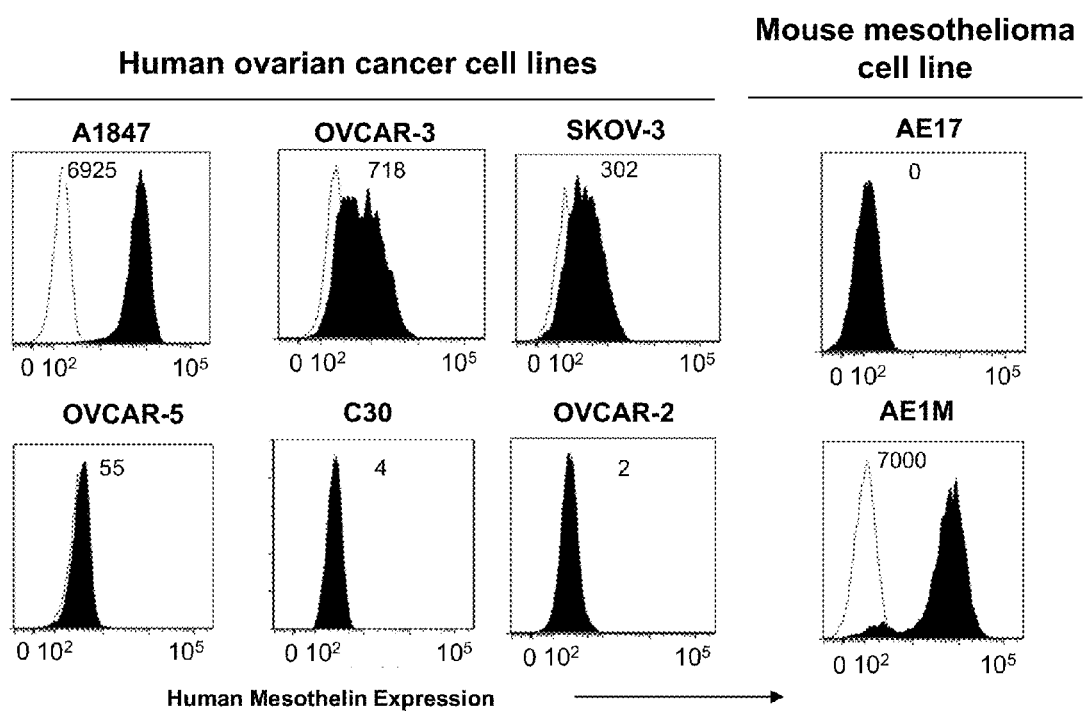
Figure 2C:
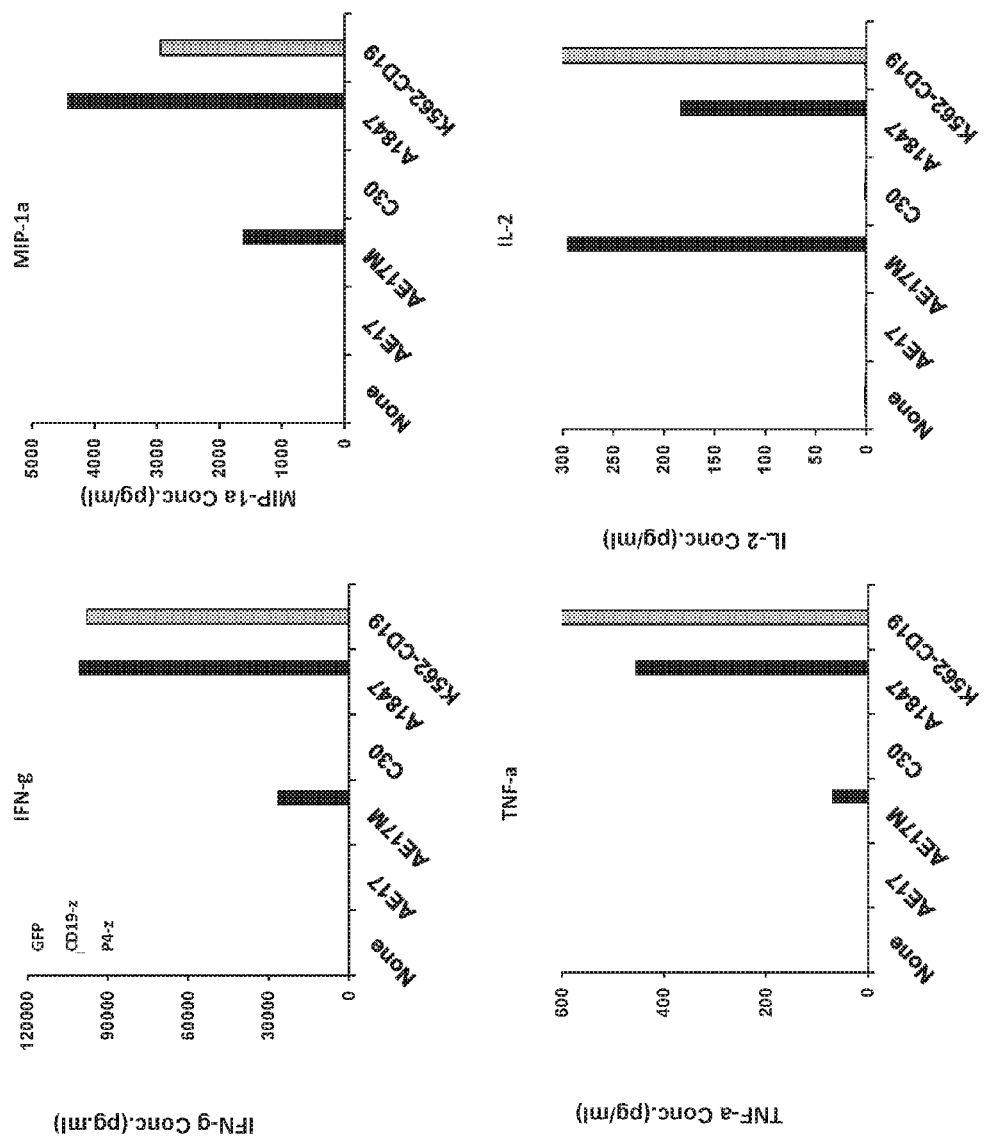
Figure 2D:
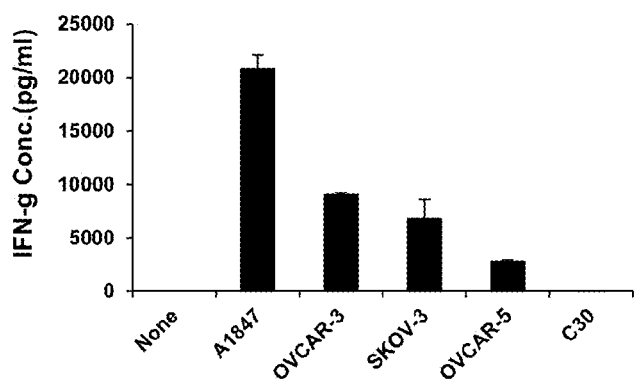
Figure 2E:
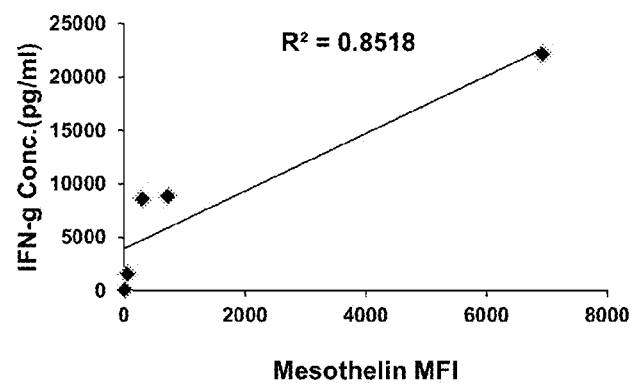

Experiments were performed to first test whether soluble or immobilized mesothelin protein stimulation induces P4-z CAR transduced T cell activation in vitro. Soluble mesothelin protein did not induce activation of P4 CAR T cells, even at high protein concentrations (5 ug/ml). However, cross-linking of the CAR by immobilized mesothelin protein resulted in robust T cell activation and secretion of high levels of IFN-γ (FIG. 2A). To evaluate the ability of P4-z CAR T cells to respond to mesothelin expressed on the cell surface, AE17, a mouse malignant mesothelioma cell line, was modified to express human mesothelin (AE17M; FIG. 2b) (Jackaman, et al., 2003, J Immunol 171: 5051-5063). P4-z CART cells secreted IFN-γ in response to AE17M cells, but not to parental AE17 cells (FIG. 2C). Since ovarian cancers frequently express mesothelin (Hassan, et al., 2005, Appl Immunohistochem Mol Morphol 13: 243-247), a panel of established human ovarian cancer cell lines of disparate HLA-haplotype that expressed surface mesothelin at varying levels (A1847, OVCAR-3, SKOV-3, OVCAR-5) or not at all (C30 and OVCAR-2) was assembled for functional assays (FIG. 2B). P4-z CAR transduced T cells secreted IFN-γ, MIP-1α, TNF-α and IL-2 in response to mesothelin+ tumor lines stimulation, but not when stimulated with mesothelin$^{neg}$ lines (FIG. 2C). Low levels of IL-4 (<25 pg/ml) and higher levels of IL-10 (<700 pg/ml) were secreted by P4 CAR T cells in response to mesothelin expressing cancer cells. P4-z CAR T cells recognized and responded to stimulation by all human ovarian cancer cells expressing detectable mesothelin on their surface (FIG. 2D). The amount of IFN-γ secreted correlated with the level of surface protein expressed by tumor cells (FIG. 2E). Control T cells transduced to express green fluorescent protein (GFP) or the CD19-z CAR did not produce cytokines after mesothelin+ tumor stimulation, demonstrating the need for antigen-specificity.

Primary Human P4 CAR T Cells Exhibit Potent Cytolytic Function

Figure 7:
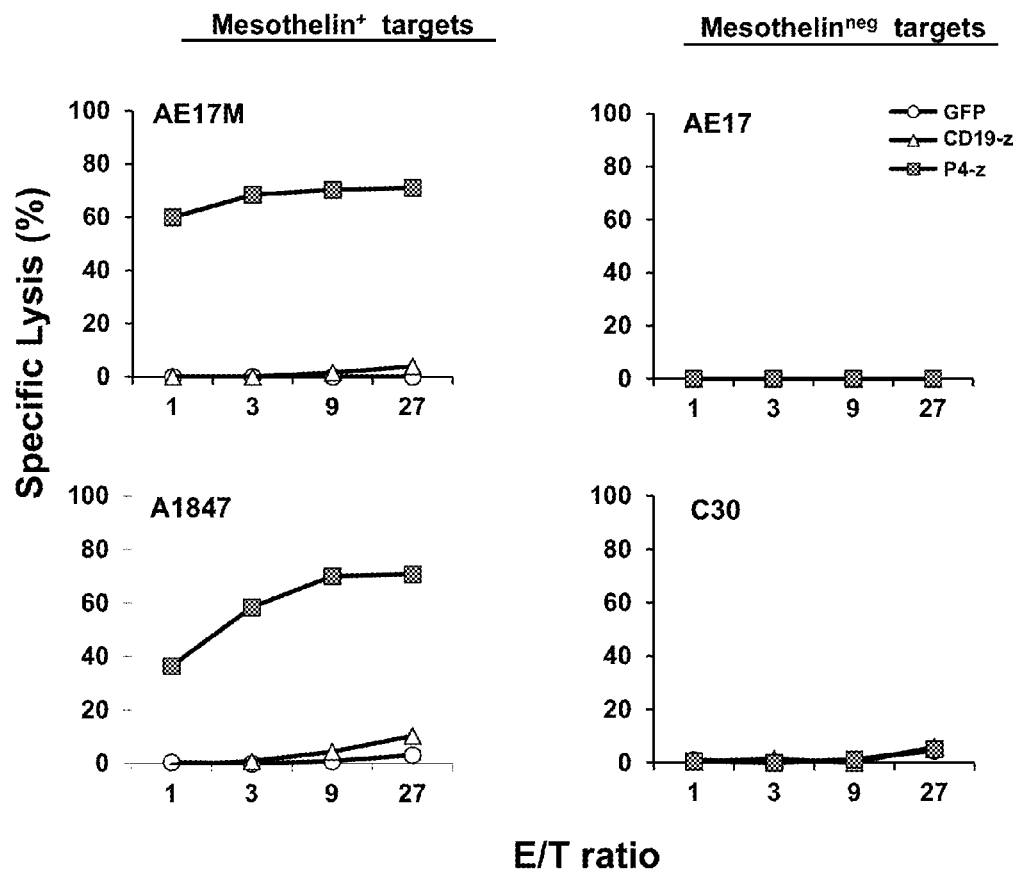
FIG. 7 is an image demonstrating antigen-specific killing of mesothelin-positive or -negative tumor cells by P4 CAR T cells in 18 h co-culture system. Co-culture of primary human T cells transduced to express either P4-z or anti-CD19-z CARs or green fluorescent protein (GFP) with $Cr^{51}$-labeled native AE17, AE17M, A1847 and C30 cell lines was extended to 18 hrs at the indicated effector to target cell ratio. Percent specific target cell lysis was calculated as (experimental−spontaneous release)÷(maximal−spontaneous release)×100. Bars indicate standard deviation.
Figure 8:
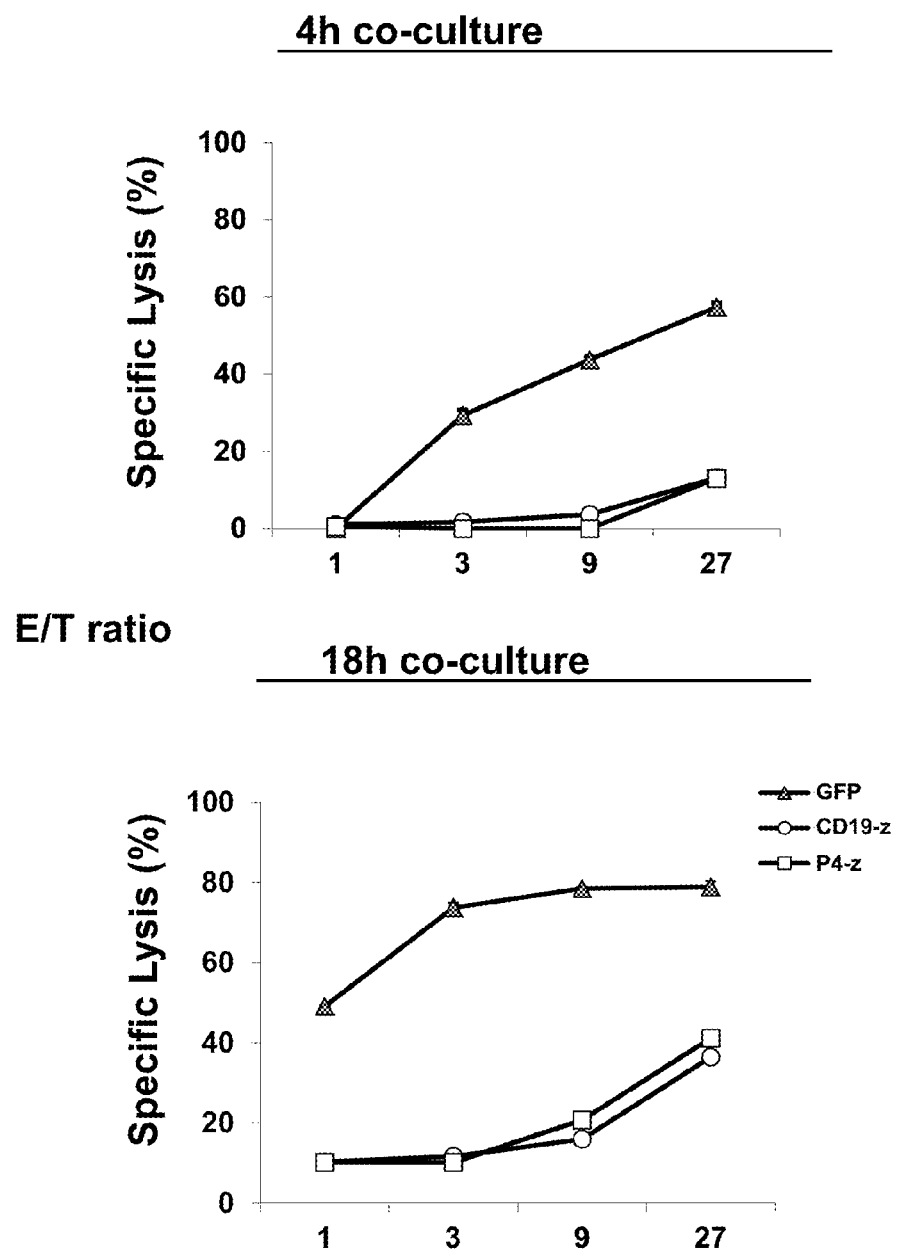
FIG. 8 is an image demonstrating antigen-specific killing of CD19+ targets by anti-CD19 CAR T cells 4 and 18 hrs post co-culture. P4-z or anti-CD19-z CARS or green fluorescent protein (GFP) T cells were co-cultured with $Cr^{51}$-labeled native K562-CD19 cells for 4 and 18 hrs at the indicated effector to target cell ratio. Percent specific target cell lysis was calculated as (experimental−spontaneous release)÷(maximal−spontaneous release)×100. Bars indicate standard deviation.

Degranulation is a quantitative indicator of lytic function by T cells (Betts, et al., 2003, J Immunol Methods 281: 65-78). P4 CAR CD8+ T cells degranulated in response to ovarian cancer cell lines expressing mesothelin (A1847, OVCAR-3, SKOV-3) or AE17M, with upregulated surface co-expression of mobilized CD107 (Lysosomal-associated membrane protein 1) and the activation-associated marker CD69, but not when stimulated with mesothelin$^{neg}$ lines (AE17 and OVCAR-2; FIG. 3a). AE17M stimulation reproducibly resulted in moderate CD107 upregulation and substantial apoptosis of CART cells. CD107 expression was restricted to T cells expressing the P4 chimeric receptors. Mock-T cells and anti-CD19 CAR T cells did not degranulate in response to mesothelin cells. In 4 hr chromium release assays, P4-z CAR T cells specifically lysed AE17M cells but not the parental AE17 line (FIG. 3B). P4-z CAR T cells also directly and efficiently lysed the mesothelin+ human ovarian cancer cell line A1847, but not mesothelin$^{neg}$ C30 cells (FIG. 3B). CD19-z CAR or GFP transduced T cells showed no cytotoxic activity against the same target cells, excluding alloreactivity or nonspecific lysis. These results were reproducible in extended 18 hour assays, with increased specific lysis from P4 CART cells (FIG. 7). Anti-CD19 CAR T cells did however lyse CD19+K562 cells, demonstrating their capacity to respond (FIG. 8).

Figure 4A:
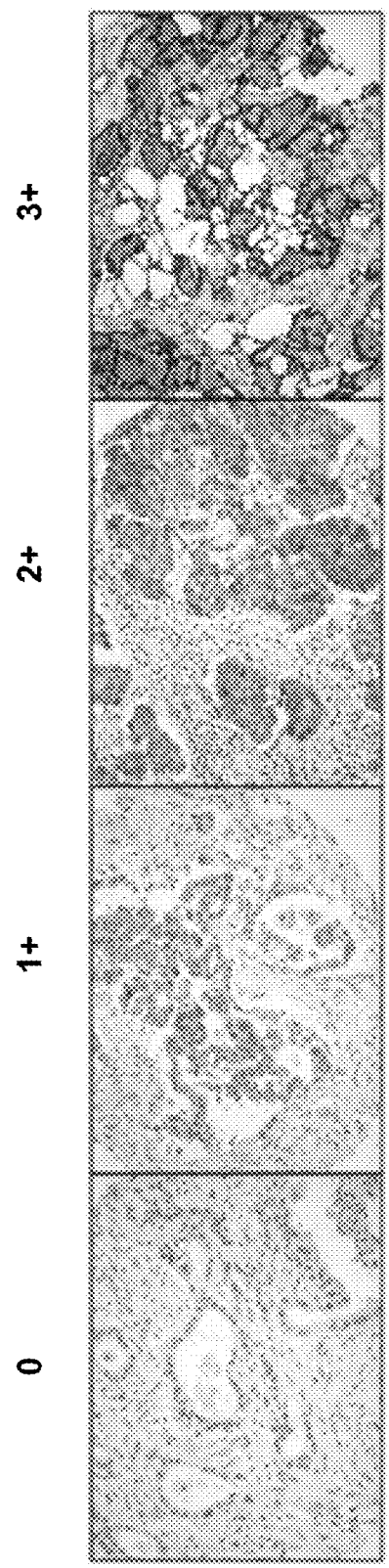
FIGS. 4A through 4C, is a series of images demonstrating bystander killing induced by P4-redirected T cells.
Figure 4B:
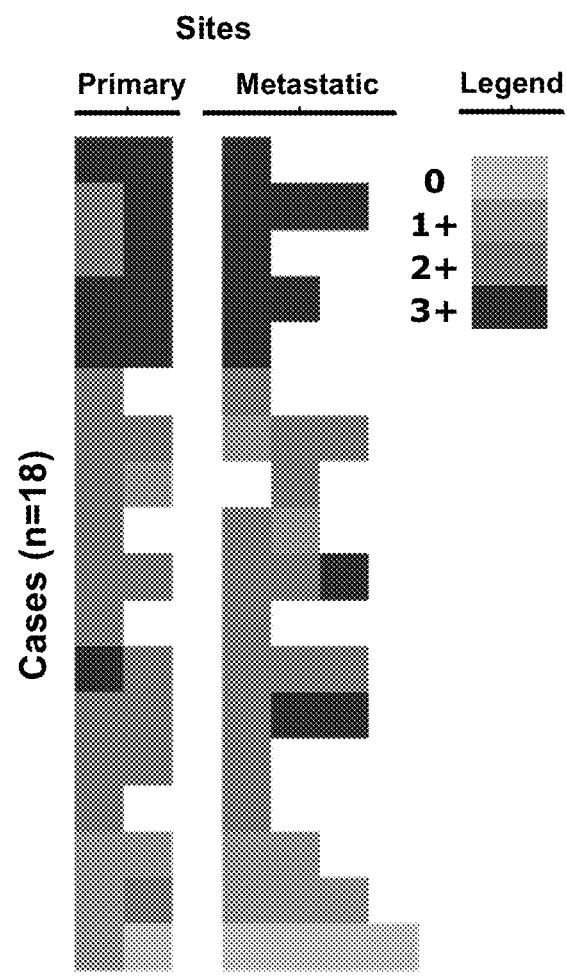
Figure 4C:
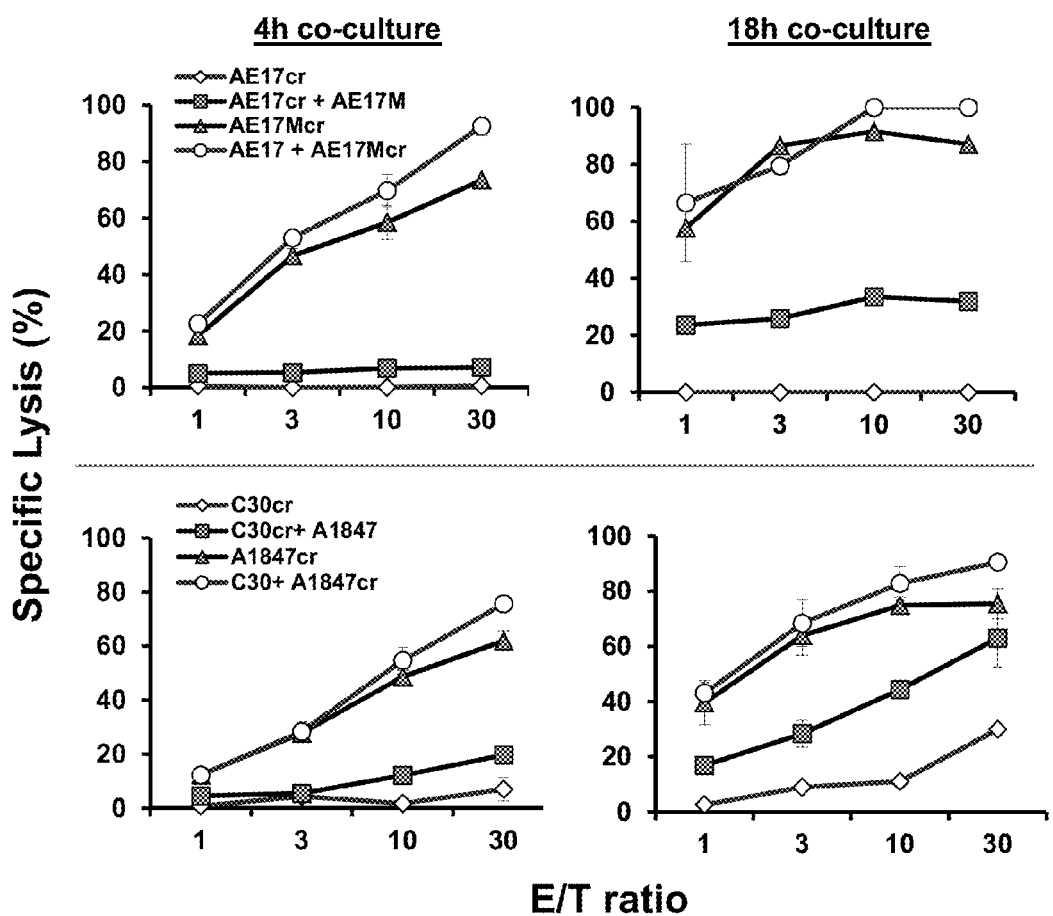
Figure 9A:
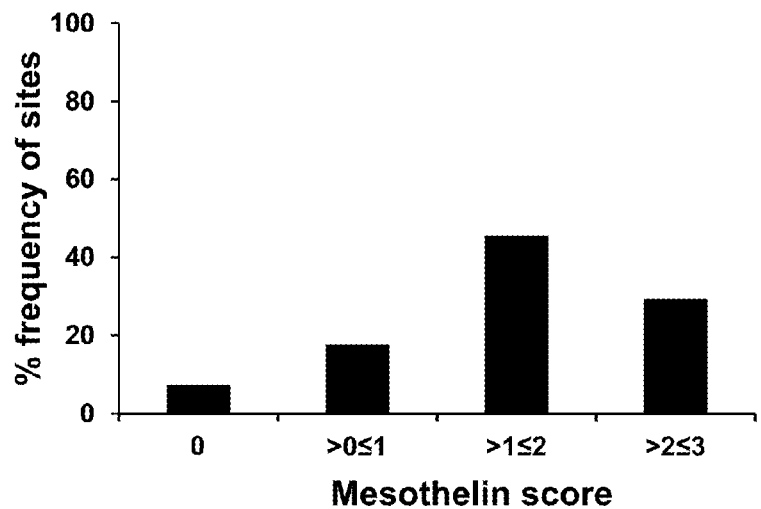
FIGS. 9A and 9B, is a series of images demonstrating expression levels of mesothelin protein among the different ovarian adenocarcinoma sites in individual cases.
Figure 9B:
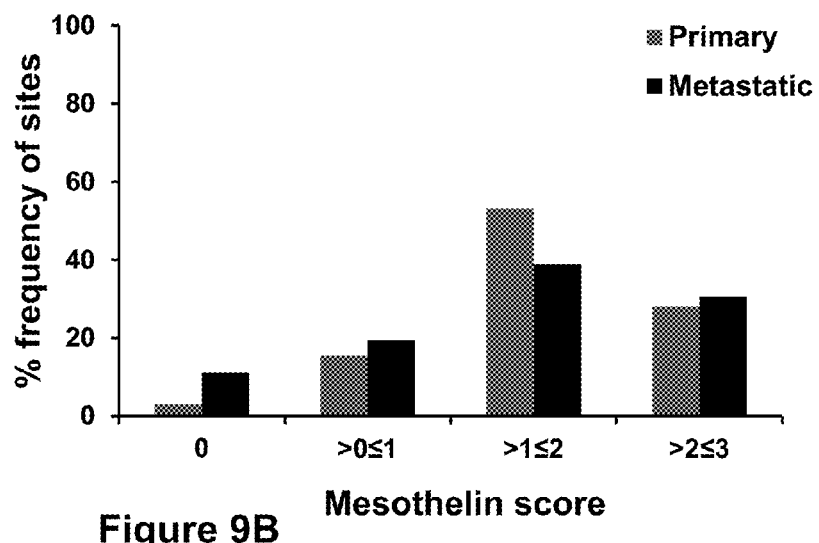
Figure 10A:
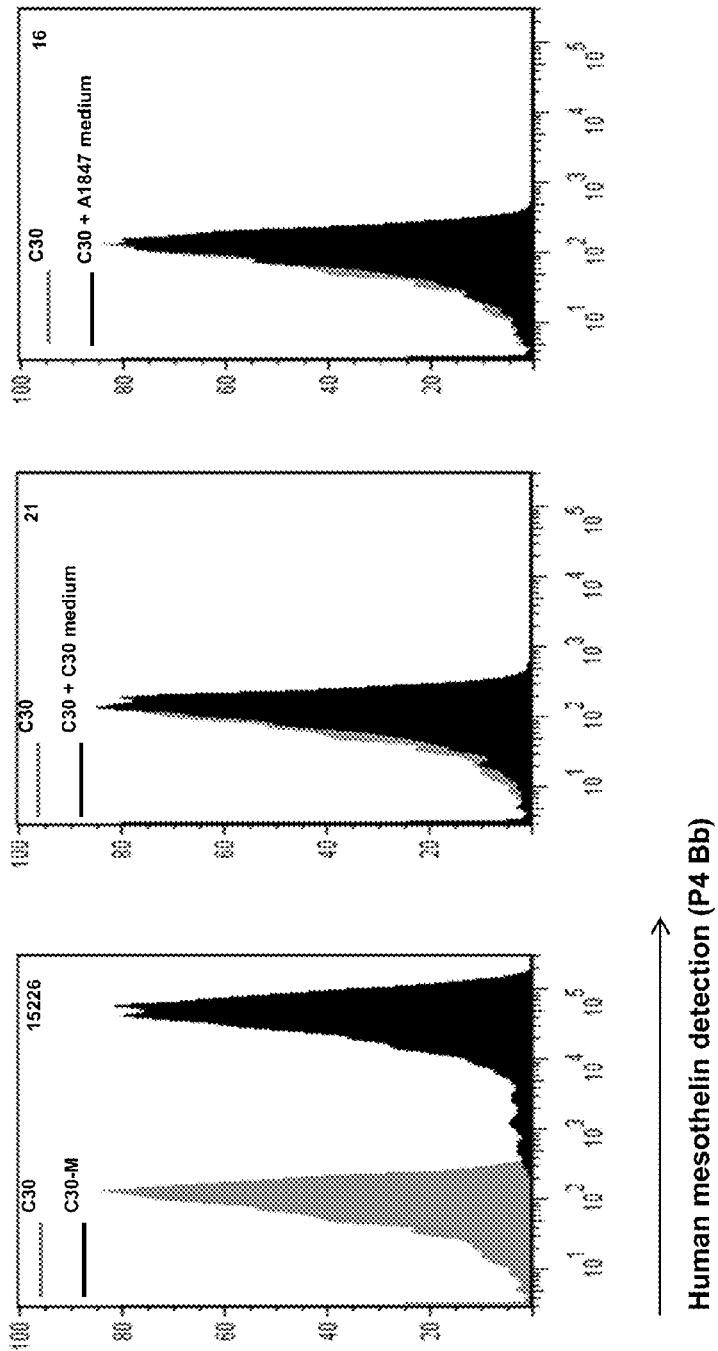
FIGS. 10A through 10C, is a series of images demonstrating that mesothelin is not transferred from antigen-positive to antigen negative cells.
Figure 10B:
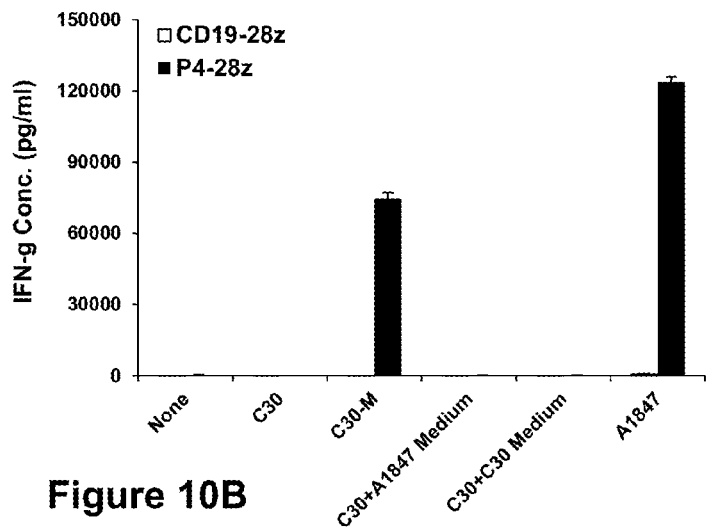
Figure 10C:
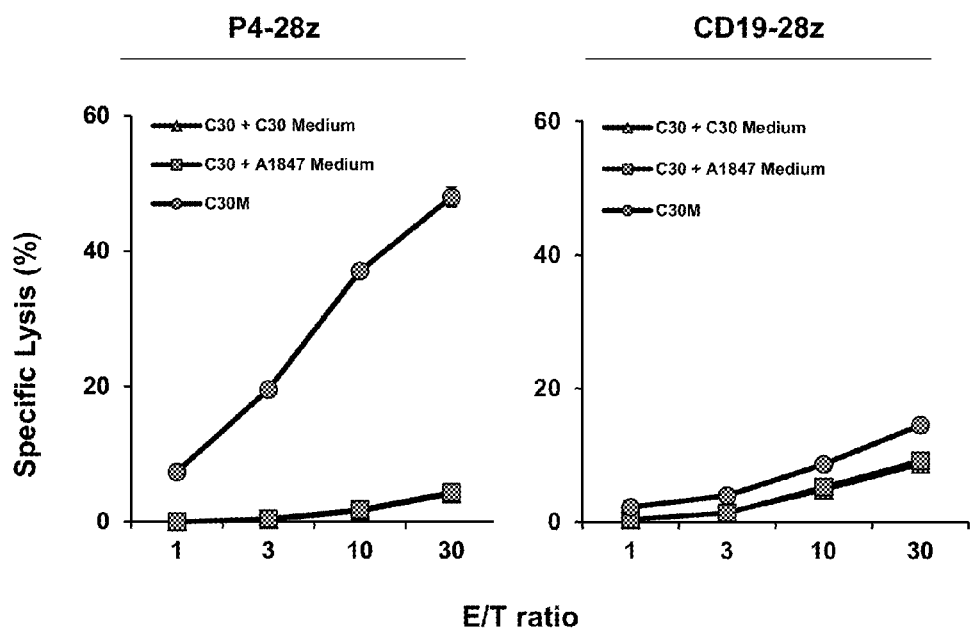

Anti-Mesothelin CAR T Cells Mediate Bystander Killing of Mesothelin-Negative Tumor Cells Since established cell lines may not accurately represent the heterogeneity of complex solid tumor samples, mesothelin expression was evaluated using immunohistochemical analysis in 18 cases of high-grade ovarian serous carcinomas in a tissue microarray. All cases contained at least one primary lesion and one metastatic site. Mesothelin was expressed at various levels among the tumor sites, ranging from undetectable (score 0) to strong staining (score 3+; FIG. 4A). Mesothelin was expressed in at least one primary site in all (18/18) cases (FIG. 4B), and 94% (17/18) of cases showed mesothelin expression at all primary and metastatic sites. Of all sites, 93% (63/68) expressed mesothelin at some level, and mesothelin scores were generally similar across metastatic and primary sites (FIG. 9). Heterogeneity in the expression levels of mesothelin protein among the different sites was present in 56% (10/18) of cases. Consistent with existing data (Yen, et al., 2006, Clin Cancer Res 12: 827-831), regional diversity in mesothelin expression level was observed, with some areas of tumor being devoid of detectable mesothelin expression, suggesting that cancer cells in these regions may be resistant to the direct cytotoxic effects of P4 CART cells. Antigen-negative tumor cells (C30 and AE17) were therefore labeled with chromium and co-cultured with P4 CAR T cells in the presence or absence of mesothelin+ tumor cells (A1847 and AE17M) to evaluate whether P4 CAR T cells can elicit bystander killing of mesothelin tumor cells. No killing of mesothelin-negative cells was detected after 4 hrs in either the presence or absence of mesothelin+ tumor cells (FIG. 4C). However, after 18 hrs of co-culture, bystander killing of the mesothelin tumor cells by P4 CAR T cells was detected but only in the presence of mesothelin+ tumor targets (FIG. 4C). In A1847 human tumor cell cultures, bystander killing was T cell dose dependent. Importantly, the level of chromium released by bystander killing substantially exceeded the level of spontaneous release in control cultures of tumor alone, excluding the likelihood of chromium reuptake by mesothelin cancer cells. Direct killing of mesothelin+ targets by P4 CAR T cells was also observed and was not inhibited by the presence of mesothelin$^{neg}$ targets. Lastly the bystander effects observed were not due to tumor-secreted mesothelin transfer from antigen-positive to antigen-negative cells (FIG. 10).

Figure 5A:
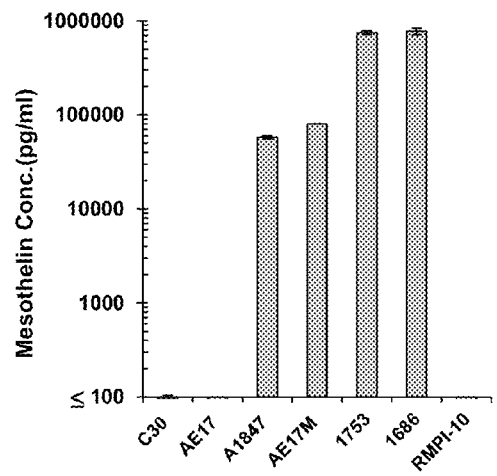
FIGS. 5A through 5D, is a series of images demonstrating that P4 CAR T cells exhibit effector functions against tumor cells in the presence of recombinant or tumor-derived mesothelin.
Figure 5B:
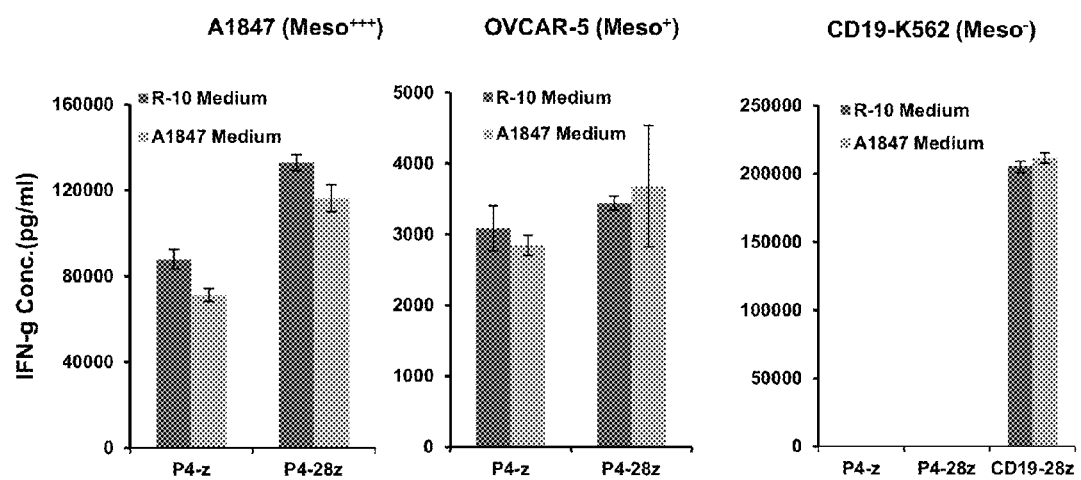
Figure 5C:
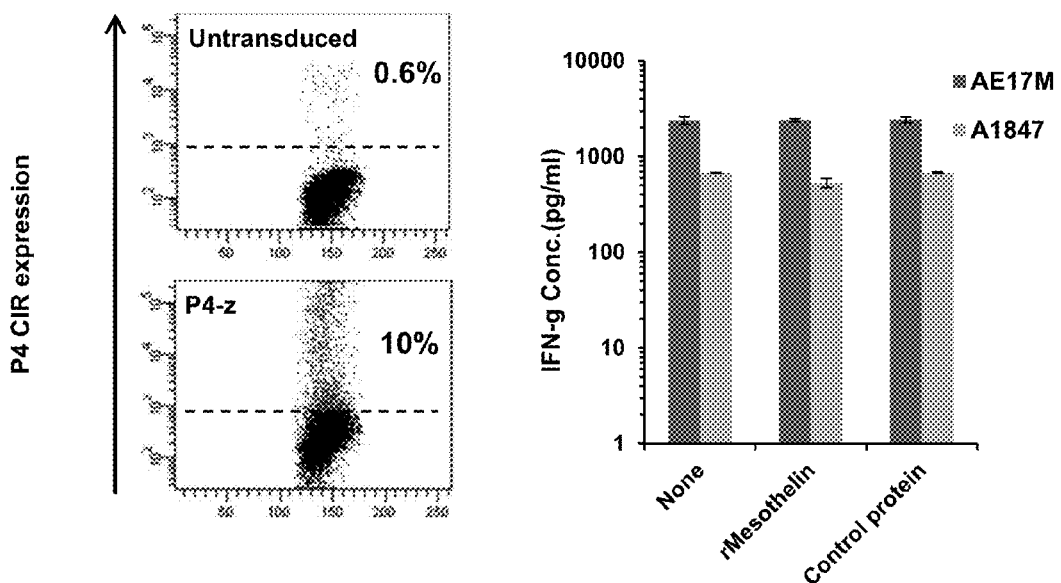

Tumor-Stimulated Response by P4 CAR T Cells is not Inhibited by Tumor-Secreted Mesothelin Ovarian cancers secrete high levels of soluble mesothelin protein which is frequently found in the serum and ascites fluid of patients, and represents a biomarker of disease (Scholler, et al., 1999, Proc Natl Acad Sci USA 96: 11531-11536; Hassan, et al., 2006, Clin Cancer Res 12: 447-453; Hellstrom, 2008, Biochem Biophys Res Commun 376: 629). Consistent with these results, high levels of soluble mesothelin (~1 ug/mL) was found in ascites fluid collected from patients with EOC (FIG. 5A). High levels of soluble mesothelin were also secreted by cancer cell lines expressing surface mesothelin (A1847 and AE17M), but not mesothelin$^{neg}$ cells (C30 and AE17), in overnight culture (FIG. 5A). To determine whether soluble mesothelin blocks P4 CAR T cell activity, co-cultures were established in the presence or absence of tumor-secreted mesothelin from cell-free A1847 tumor supernatants (~25 ng/mL final concentration). First (P4-z) or second generation (P4-28z) CART cells co-cultured with mesothelin$^+$ A1847 cells retained their IFN-γ response in the presence of tumor-derived soluble mesothelin (FIG. 5B). Similar results were observed from co-cultures of P4 CART cells and OVCAR-5 as target cells, which are mesothelin$^{low}$ (FIG. 2B). CD19-redirected T cells also retained their activity against CD19$^+$K562 target cells in the presence of soluble mesothelin protein. Additional co-culture assays of P4-z CART cells with mesothelin+ cancer cells (A1847 and AE17M) were performed in the presence of recombinant mesothelin protein at supraphysiological levels (5 ug/ml); 5-fold higher concentrations than that measured in patient-derived ascites fluid (FIG. 5A). To more rigorously assess blocking capacity, P4 CART cells were also diluted 10-fold with untransduced T cells prior to co-culture to reduce their frequency to 10% of total T cells (FIG. 5C). Again, no blocking of P4 CART cell tumor recognition and IFN-γ secretion by recombinant mesothelin protein was detected (FIG. 5C). Control protein at identical concentration also did not block T cell responses.

Figure 5D:
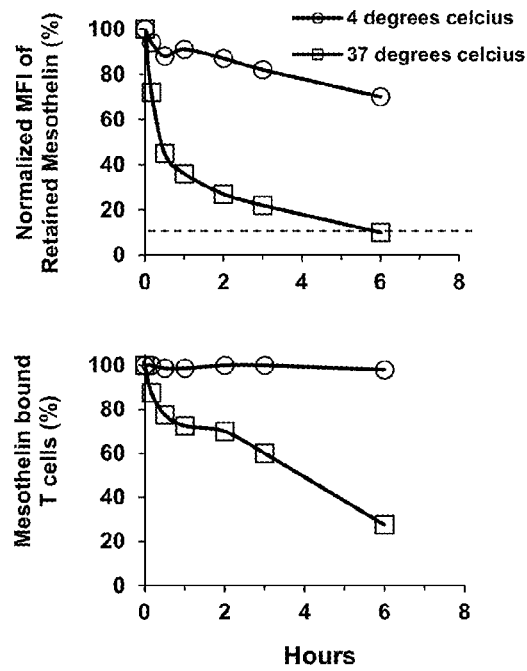

The next experiments were performed to longitudinally measure by flow cytometry the dissociation of biotinylated-mesothelin protein that was pre-bound to P4-z CAR T cells in the presence of 10-fold higher concentration of unbiotinylated protein and incubated at either 37° C. or 4° C., as a surrogate indicator of CAR affinity. A modest dissociation of biotinylated mesothelin (30%) was detected over 6 hours at 4° C. based upon mean fluorescence intensity (MFI), although all CAR T cells remained bound at some level (FIG. 5D). At 37° C. progressive, substantial loss of detectable surface protein was evident within 10 minutes and fully displaced to background levels (90%) after 6 hours, showing the transient nature of P4 CAR binding to soluble mesothelin protein under standard culture conditions that may provide the opportunity for CAR re-engagement with surface bound antigen.

Figure 6A:
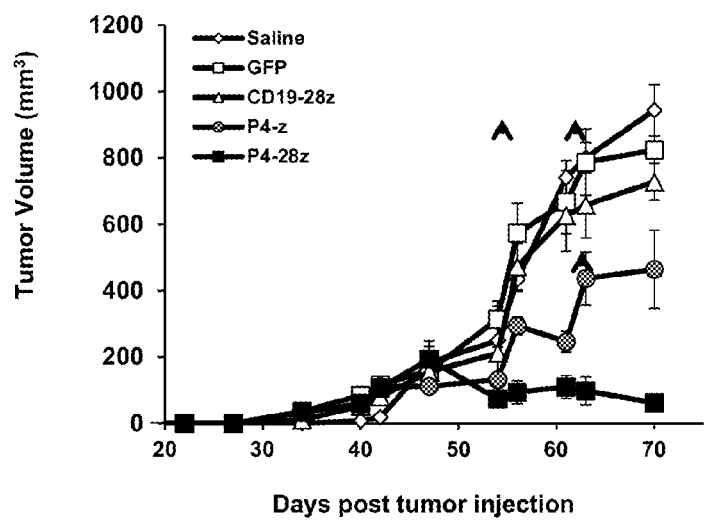
Figure 6B:
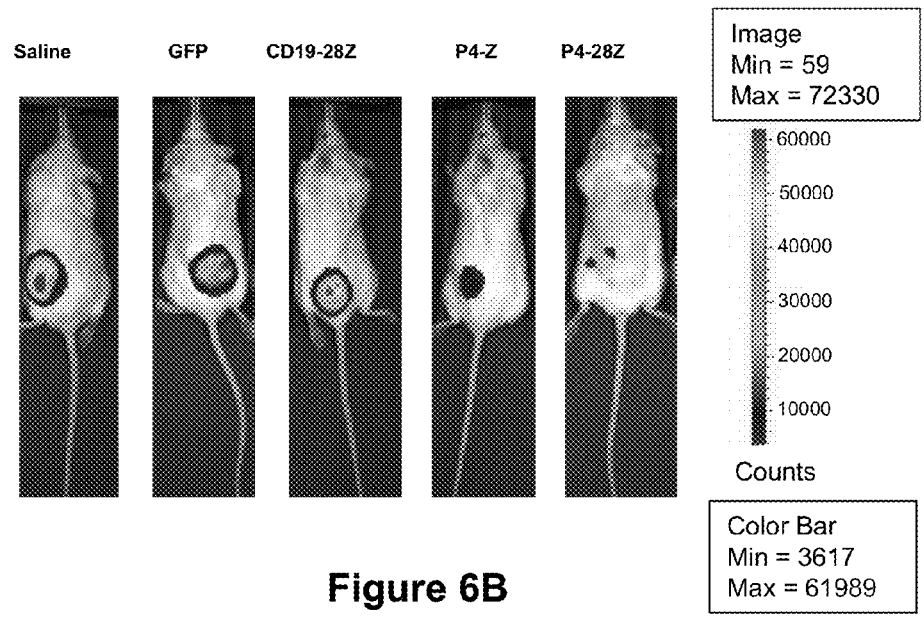
Figure 11C:
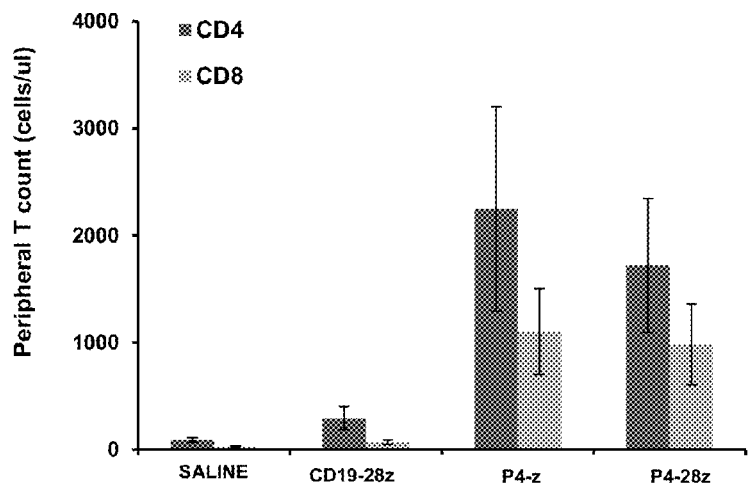
Figure 11D:
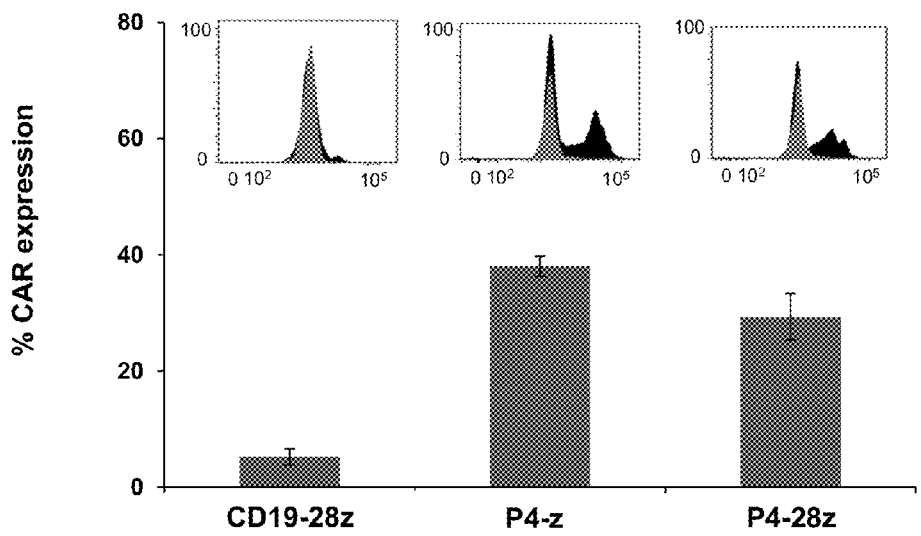

Antitumor Activity of Primary Human T Cells Expressing P4 Anti-Mesothelin CAR in Vivo To evaluate the capacity of P4 CART cells to induce regression of large, established human tumors in vivo, second generation P4-28z CAR T cells were used since it has been previously shown that costimulated CAR T cells exhibit enhanced effector functions in vivo (Alvarez-Vallina, et al., 1996, Eur J Immunol 26: 2304-2309; Kowolik, et al., 2006, Cancer Res 66: 10995-11004; Beecham, et al., 2000, J Immunother 23: 631-642). P4-28z CART cells used for infusion showed specific and enhanced IFN-γ secretion as well as IL-2 and TNF-α in response to mesothelin$^+$ tumor stimulation in vitro, compared with P4-z CAR T cells, confirming their functional reactivity (FIGS. 11A and 11B). NSG mice with established s.c. A1847 tumors (≥150 mm$^3$) received intratumoral injections of CART cells on days 47 and 57 post-tumor inoculation. Tumor growth was modestly inhibited in mice receiving P4-z CAR T cells (P=0.07), compared to saline, CD19-28z CAR T cells or GFP T cell control groups 3 weeks after first T cell dose (FIG. 6A). In contrast, mice receiving P4-28z T cells experienced rapid tumor regression which was significantly better than P4-z T cells (P<0.05), indicating that incorporation of CD28 signals enhances net anti-tumor activity in vivo (FIGS. 6A and 6B). Furthermore a xenogeneic model of advanced intraperitoneal metastatic cancer was established to evaluate the functional activity of P4 CART cells against tumor in a more physiologically relevant compartment. NSG mice were inoculated i.p. with A1847 fLuc$^+$ cells. Two weeks post-inoculation, two i.v. injections of P4-28z T cells resulted in rapid tumors regression in all mice (FIGS. 6c and d). Disease progression occurred in all mice receiving CD19-28z T cells. Mice treated with P4-28z CAR did not develop distended abdomens or ascites, and exhibited a profound enhancement in tumor-related survival (p<0.05) with no cases of tumor-related mortality. In the CD19-28z control group, all mice had to be euthanized due to disease progression 30-45 days post first T cell infusion. Three weeks after the first T cell dose, peripheral blood CD8$^+$ T and CD4$^+$ T cell counts from mice injected with P4-28z T cells were significantly higher than in the CD19-28z group (p<0.05; FIG. 6E). Mice that received P4-28z CART cell transfer also had increased persistence of human T cells bearing surface scFv (57%), compared to CD19-28z CART cell treated mice (0.82%; FIG. 6F). Similar differences in blood counts and CAR expression were observed in mice with s.c. tumors (FIGS. 11C and 11D).

Primary Human T-Cells Expressing a Fully Human CAR Targeting Mesothelin are Highly Effective To date, only one other mesothelin-specific CAR has been reported (Carpenito, et al., 2009, Proc Natl Acad Sci USA 106: 3360-3365), the SS1 CAR, whose specificity is derived from the mouse anti-human mesothelin scFv SS1 (Chowdhury, et al., 1998, Proc Natl Acad Sci USA 95: 669-674). SS1 CART cells exert potent effector functions against cancer cell lines expressing mesothelin in vitro and eradicate established mesotheliomas in preclinical studies (Carpenito, et al., 2009, Proc Natl Acad Sci USA 106: 3360-3365). Two Phase I studies (Kreitman, et al., 2009, Clin Cancer Res 15: 5274-5279; Hassan, et al., 2007, Clin Cancer Res 13: 5144-5149) of SS1 coupled to Pseudomonas Exotoxin A (PE38) have shown anti-tumor activity in subjects with mesothelin$^+$ tumors and a chimeric antibody based on SS1 scFv (MORAb-009) remains under investigation in a Phase II study for mesothelioma and pancreatic cancer. Still, human anti-mouse antibody (HAMA) responses have not been assessed in these SS1-treated subjects. However, the mouse origin of the SS1 scFv predicts its propensity for inducing xenogeneic responses upon transfer to human subjects.

The immunogenicity of mouse transgenes is noted in numerous trials of adoptive immunotherapy using autologous T cells modified to express mouse-derived scFvs or tumor antigen-specific T cell receptors (TCRs) (Kershaw, et al., 2006, Clin Cancer Res 12: 6106-6115; Lamers, et al., 2011, Blood 117: 72-82; Lamers, et al., 2007, Cancer Immunol Immunother 56: 1875-1883; Lamers, et al., 2006, J Clin Oncol 24: e20-22). Transfer of T cells outfitted with xenogeneic CARs to immunocompetent subjects induces transgene-specific immune responses, which may limit the persistence and function of the gene-modified cells (Kershaw, et al., 2006, Clin Cancer Res 12: 6106-6115; Lamers, et al., 2007, Cancer Immunol Immunother 56: 1875-1883; Lamers, et al., 2006, J Clin Oncol 24: e20-22). Humoral responses are often noted. Induction of both humoral and cellular immune responses has been reported in patients treated with ex vivo-engineered anti-CAIX CAR T cells (Lamers, et al., 2011, Blood 117: 72-82). Such responses were directed against the xenogeneic complementarity-determining and framework regions of the CAR variable domains. While lymphodepleting chemotherapy can transiently disable endogenous T and B cell responses, transfer of autologous T cells bearing a murine anti-CEA TCR to patients with metastatic colorectal cancer after lymphodepleting pre-conditioning still induced anti-mouse TCR-specific IgG antibodies that was capable of impairing the functionality of CEA-specific TCR T cells in vitro (Parkhurst, et al., 2011, Mol Ther 19: 620-626).

The CAR constructs discussed herein utilizes the human anti-mesothelin P4 scFv, originally developed by selective enrichment of a yeast-display human scFv library (Feldhaus, et al., 2003, Nat Biotechnol 21: 163-170), which demonstrates high specificity with binding of Meso-Ig protein detectable in the range of ng/ml (Bergan, et al., 2007, Cancer Lett 255: 263-274).

An important issue concerning antibody-based therapies directed against mesothelin is the stimulatory or possible inhibitory effect of soluble antigen on the ability to target membrane-bound mesothelin, particularly in ovarian cancer patients where high levels of soluble mesothelin is present in serum or ascites fluid (Scholler, et al., 1999, Proc Natl Acad Sci USA 96: 11531-11536; Hassan, et al., 2006, Clin Cancer Res 12: 447-453; Hellstrom, 2008, Biochem Biophys Res Commun 376: 629). Immobilized mesothelin protein was able to activate P4 CAR T cells, a feature not detectable when soluble mesothelin was used. Until now, resistance of anti-mesothelin CAR T cells has not been tested. P4 CAR T cells challenged with ovarian cancer cells expressing high or low levels of mesothelin resisted functional inhibition by soluble mesothelin protein, even at supraphysiological levels. Resistance was confirmed by their capacity to mediate the regression of established tumors in vivo in the presence of high levels of cancer-secreted mesothelin in the serum of treated mice (59 ng/ml±2.87 ng/ml, n=3, data not shown). The results presented herein expand upon prior reports (Westwood, et al., 2009, J Immunother 32: 292-301; Hombach, et al., 1998, Cancer Res 58: 1116-1119; Nolan, et al., 1999, Clin Cancer Res 5: 3928-3941), and suggest a CAR's ability to resist soluble antigen blockade lies in its ability to disengage soluble antigen at physiological temperature, and the need for cross-linking of a critical mass of CAR receptors on the T cell surface which is provided by immobilized, but not soluble, mesothelin protein.

The P4 anti-mesothelin CAR allows for the direct cytolytic destruction of antigen-positive tumor cells, however tumor antigens are often heterogeneously expressed amongst particular cancer histologies. The immunohistochemical analysis of multiple serous adenocarcinoma tumor sections reveals disparate regional mesothelin expression with little to no detectable mesothelin expression in certain tumor areas. It was observed that that antigen-activated P4 CAR T cells may exert effector functions capable of inducing bystander killing of cancer cells not expressing the target antigen. Soluble factors released by CAR-activated effector cells are indeed able to inhibit tumor growth of tumor cells lacking a cognate antigen (Turatti, et al., 2005, J Gene Med 7: 158-170). The results presented herein suggest that antigen-less tumor cells within a heterogeneous field of mesothelin-expressing tumor may be susceptible to indirect destruction by mesothelin-redirected T cells that has previously reacted against adjacent antigen-positive cancer cells. However, bystander activity may cause damage to the surrounding normal tissue. Thus, fine-tuning of CAR specificity and activity is desirable.

P4 CAR T cells control large, well-established tumors in immunodeficient mice. Consistent with multiple reports (Carpenito, et al., 2009, Proc Natl Acad Sci USA 106(9): 3360-5; Milone, et al., 2009, Mol Ther 17: 1453-1464), first generation CAR possessing only CD3z signaling had modest impact on tumor outgrowth in vivo while second generation CAR comprising CD3z fused to a CD28 costimulatory domain mediated tumor regression in vivo (Kowolik, et al., 2006, Cancer Res 66: 10995-11004). T cells modified to express an irrelevant anti-CD19 CAR or GFP were unable to alter tumor growth demonstrating the high specificity of the CAR system and ruling out the possibility of xenogeneity as the source of the tumor response. Persistence of human T cells was highest in mice treated with P4 CARs compared with control CD19-28z T cells demonstrating that antigen exposure is sufficient to support preferential CAR transduced T cell engraftment and persistence in vivo. However, the persistence of P4 CART cells was independent of the addition of the CD28 costimulatory domain, as noted previously (Carpenito, et al., 2009, Proc Natl Acad Sci USA 106(9): 3360-5).

The results presented herein show that primary human T-cells expressing a fully human CAR targeting mesothelin are highly effective in response controlling large, well-established tumors. While the safety and efficacy of mesothelin-directed CAR therapy has yet to be tested in the clinic, the fully-human P4 CAR described here is well-positioned to resist soluble protein inhibition, elude transgene immunogenicity and maximize anti-tumor efficacy of adoptively transferred T cells in vivo.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated nucleic acid sequence encoding a chimeric antigen receptor (CAR), wherein the isolated nucleic acid sequence encodes an amino acid sequence selected from the group consisting of SEQ ID NO: 3, SEQ ID NO: 5, and SEQ ID NO: 7.

2. The isolated nucleic acid sequence of claim 1 comprising the nucleic acid sequence selected from the group consisting of SEQ ID NO: 4, SEQ ID NO: 6, and SEQ ID NO: 8.

3. An isolated chimeric antigen receptor (CAR) comprising an amino acid sequence selected from the group consisting of SEQ ID NO: 3, SEQ ID NO: 5, and SEQ ID NO: 7.

4. The isolated CAR of claim 3 encoded by a nucleic acid sequence selected from the group consisting of SEQ ID NO: 4, SEQ ID NO: 6, and SEQ ID NO: 8.

5. A genetically modified cell comprising an isolated nucleic acid sequence encoding a chimeric antigen receptor (CAR), wherein the isolated nucleic acid sequence encodes an amino acid sequence selected from the group consisting of SEQ ID NO: 3, SEQ ID NO: 5, and SEQ ID NO: 7.

6. The genetically modified cell of claim 5, wherein the isolated nucleic acid comprises a nucleic acid sequence selected from the group consisting of SEQ ID NO: 4, SEQ ID NO: 6, and SEQ ID NO: 8.

7. The genetically modified cell of claim 5, wherein the cell is a T cell.

8. The genetically modified cell of claim 5, wherein the cell exhibits an anti-tumor immunity when the cell is cross-linked with a mesothelin protein.

9. A method of providing an anti-tumor immunity in a mammal, the method comprising administering to the mammal an effective amount of a genetically modified cell comprising an isolated nucleic acid sequence encoding a chimeric antigen receptor (CAR), wherein the isolated nucleic acid sequence encodes an amino acid sequence selected from the group consisting of SEQ ID NO: 3, SEQ ID NO: 5, and SEQ ID NO: 7.

10. The method of claim 9, wherein the cell is an autologous T cell.

11. The method of claim 9, wherein the mammal is a human.

12. A method of treating a mammal having a disease, disorder or condition associated with dysregulated expression of mesothelin, the method comprising administering to the mammal an effective amount of a genetically modified cell comprising an isolated nucleic acid sequence encoding a chimeric antigen receptor (CAR), wherein the isolated nucleic acid sequence encodes an amino acid sequence selected from the group consisting of SEQ ID NO: 3, SEQ ID NO: 5, and SEQ ID NO: 7.

13. The method of claim 12, wherein the disease, disorder or condition associated with dysregulated expression of mesothelin is selected from the group consisting of mesothelioma, pancreatic cancer, ovarian cancer, stomach cancer, lung cancer, endometrial cancer, and any combination thereof.

* * * * *

SEQUENCE LISTING

```
<160> NUMBER OF SEQ ID NOS: 24

<210> SEQ ID NO 1
<211> LENGTH: 29
<212> TYPE: DNA
<213> ORGANISM: Artificial
<220> FEATURE:
<223> OTHER INFORMATION: Chemically synthesized

<400> SEQUENCE: 1
```

```
gcgagatctc aggtacagct gcagcagtc                                         29
```

<210> SEQ ID NO 2
<211> LENGTH: 29
<212> TYPE: DNA
<213> ORGANISM: Artificial
<220> FEATURE:
<223> OTHER INFORMATION: Chemically synthesized

<400> SEQUENCE: 2

```
cgcgctagcg gagaggacgg tcagttggg                                         29
```

<210> SEQ ID NO 3
<211> LENGTH: 465
<212> TYPE: PRT
<213> ORGANISM: Artificial
<220> FEATURE:
<223> OTHER INFORMATION: Chemically synthesized

<400> SEQUENCE: 3

```
Met Ala Leu Pro Val Thr Ala Leu Leu Pro Leu Ala Leu Leu Leu
1               5                   10                  15

His Ala Ala Arg Pro Gly Ser Gln Val Gln Leu Gln Gln Ser Gly Pro
            20                  25                  30

Gly Leu Val Thr Pro Ser Gln Thr Leu Ser Leu Thr Cys Ala Ile Ser
        35                  40                  45

Gly Asp Ser Val Ser Ser Asn Ser Ala Thr Trp Asn Trp Ile Arg Gln
    50                  55                  60

Ser Pro Ser Arg Gly Leu Glu Trp Leu Gly Arg Thr Tyr Tyr Arg Ser
65                  70                  75                  80

Lys Trp Tyr Asn Asp Tyr Ala Val Ser Val Lys Ser Arg Met Ser Ile
                85                  90                  95

Asn Pro Asp Thr Ser Lys Asn Gln Phe Ser Leu Gln Leu Asn Ser Val
            100                 105                 110

Thr Pro Glu Asp Thr Ala Val Tyr Tyr Cys Ala Arg Gly Met Met Thr
        115                 120                 125

Tyr Tyr Tyr Gly Met Asp Val Trp Gly Gln Gly Thr Thr Val Thr Val
    130                 135                 140

Ser Ser Gly Ile Leu Gly Ser Gly Gly Gly Ser Gly Gly Gly Gly
145                 150                 155                 160

Ser Gly Gly Gly Gly Ser Gln Pro Val Leu Thr Gln Ser Ser Ser Leu
                165                 170                 175

Ser Ala Ser Pro Gly Ala Ser Ala Ser Leu Thr Cys Thr Leu Arg Ser
            180                 185                 190

Gly Ile Asn Val Gly Pro Tyr Arg Ile Tyr Trp Tyr Gln Gln Lys Pro
        195                 200                 205

Gly Ser Pro Pro Gln Tyr Leu Leu Asn Tyr Lys Ser Asp Ser Asp Lys
    210                 215                 220

Gln Gln Gly Ser Gly Val Pro Ser Arg Phe Ser Gly Ser Lys Asp Ala
225                 230                 235                 240

Ser Ala Asn Ala Gly Val Leu Leu Ile Ser Gly Leu Arg Ser Glu Asp
                245                 250                 255

Glu Ala Asp Tyr Tyr Cys Met Ile Trp His Ser Ser Ala Ala Val Phe
            260                 265                 270

Gly Gly Gly Thr Gln Leu Thr Val Leu Ser Ala Ser Thr Thr Thr Pro
        275                 280                 285

Ala Pro Arg Pro Pro Thr Pro Ala Pro Thr Ile Ala Ser Arg Pro Leu
```

```
                290                 295                 300
Ser Leu Arg Pro Glu Ala Cys Arg Pro Ala Ala Gly Gly Ala Val His
305                 310                 315                 320

Thr Arg Gly Leu Asp Phe Ala Cys Asp Ile Tyr Ile Trp Ala Pro Leu
                325                 330                 335

Ala Gly Thr Cys Gly Val Leu Leu Leu Ser Leu Val Ile Thr Leu Tyr
                340                 345                 350

Cys Arg Val Lys Phe Ser Arg Ser Ala Asp Ala Pro Ala Tyr Gln Gln
                355                 360                 365

Gly Gln Asn Gln Leu Tyr Asn Glu Leu Asn Leu Gly Arg Arg Glu Glu
                370                 375                 380

Tyr Asp Val Leu Asp Lys Arg Arg Gly Arg Asp Pro Glu Met Gly Gly
385                 390                 395                 400

Lys Pro Arg Arg Lys Asn Pro Gln Glu Gly Leu Tyr Asn Glu Leu Gln
                405                 410                 415

Lys Asp Lys Met Ala Glu Ala Tyr Ser Glu Ile Gly Met Lys Gly Glu
                420                 425                 430

Arg Arg Arg Gly Lys Gly His Asp Gly Leu Tyr Gln Gly Leu Ser Thr
                435                 440                 445

Ala Thr Lys Asp Thr Tyr Asp Ala Leu His Met Gln Ala Leu Pro Pro
                450                 455                 460

Arg
465

<210> SEQ ID NO 4
<211> LENGTH: 1398
<212> TYPE: DNA
<213> ORGANISM: Artificial
<220> FEATURE:
<223> OTHER INFORMATION: chemically synthesized

<400> SEQUENCE: 4
atggccttac cagtgaccgc cttgctcctg ccgctggcct tgctgctcca cgccgccagg      60
ccgggatctc aggtacagct gcagcagtca ggtccaggac tcgtgacgcc ctcgcagacc     120
ctctcactca cctgtgccat ctccggggac agtgtctcta gcaacagtgc tacttggaac     180
tggatcaggc agtccccatc gagaggcctt gagtggctgg aaggacata ctacaggtcc      240 aagtggtata cgactatgc agtatctgtg aaaagtcgaa tgagcatcaa cccagacaca      300
tccaagaacc agttctccct gcagctgaac tctgtgactc ccgaggacac ggctgtgtat     360
tactgtgcaa aggaatgat gacttactat tacggtatgg acgtctgggg ccaagggacc      420
acggtcaccg tctcctcagg aattctagga tccggtggcg gtggcagcgg cggtggtggt     480
tccggaggcg gcggttctca gcctgtgctg actcagtcgt cttccctctc tgcatctcct     540
ggagcatcag ccagtctcac ctgcaccttg cgcagtggca tcaatgttgg tcctacagg      600 atatactggt accagcagaa gccagggagt cctccccagt atctcctgaa ctacaaatca     660
gactcagata agcagcaggg ctctggagtc cccagccgct tctctggatc caaagatgct     720
tcggccaatg cagggggttttt actcatctct gggctccggt ctgaggatga ggctgactat     780
tactgtatga tttggcacag cagcgctgct gtgttcggag gaggcaccca actgaccgtc     840
ctctccgcta gcaccacgac gccagcgccg cgaccaccaa caccggcgcc caccatcgcg     900
tcgcggcccc gtccctgcg cccagaggcg tgccggccag cggcggggg cgcagtgcac      960 acgagggggc tggacttcgc ctgtgatatc tacatctggg cgcccttggc cgggacttgt    1020
```

```
ggggtccttc tcctgtcact ggttatcacc ctttactgca gagtgaagtt cagcaggagc    1080
gcagacgccc ccgcgtacca gcagggccag aaccagctct ataacgagct caatctagga    1140
cgaagagagg agtacgatgt tttggacaag agacgtggcc gggaccctga gatgggggga    1200
aagccgagaa ggaagaaccc tcaggaaggc ctgtacaatg aactgcagaa agataagatg    1260
gcggaggcct acagtgagat tgggatgaaa ggcgagcgcc ggaggggcaa ggggcacgat    1320
ggcctttacc agggtctcag tacagccacc aaggacacct acgacgccct tcacatgcag    1380
gccctgcccc ctcgctaa                                                  1398

<210> SEQ ID NO 5
<211> LENGTH: 511
<212> TYPE: PRT
<213> ORGANISM: Artificial
<220> FEATURE:
<223> OTHER INFORMATION: Chemically synthesized

<400> SEQUENCE: 5
```

Met Ala Leu Pro Val Thr Ala Leu Leu Leu Pro Leu Ala Leu Leu Leu
1               5                   10                  15

His Ala Ala Arg Pro Gly Ser Gln Val Gln Leu Gln Gln Ser Gly Pro
            20                  25                  30

Gly Leu Val Thr Pro Ser Gln Thr Leu Ser Leu Thr Cys Ala Ile Ser
        35                  40                  45

Gly Asp Ser Val Ser Ser Asn Ser Ala Thr Trp Asn Trp Ile Arg Gln
    50                  55                  60

Ser Pro Ser Arg Gly Leu Glu Trp Leu Gly Arg Thr Tyr Tyr Arg Ser
65                  70                  75                  80

Lys Trp Tyr Asn Asp Tyr Ala Val Ser Val Lys Ser Arg Met Ser Ile
                85                  90                  95

Asn Pro Asp Thr Ser Lys Asn Gln Phe Ser Leu Gln Leu Asn Ser Val
            100                 105                 110

Thr Pro Glu Asp Thr Ala Val Tyr Tyr Cys Ala Arg Gly Met Met Thr
        115                 120                 125

Tyr Tyr Tyr Gly Met Asp Val Trp Gly Gln Gly Thr Thr Val Thr Val
    130                 135                 140

Ser Ser Gly Ile Leu Gly Ser Gly Gly Gly Ser Gly Gly Gly Gly
145                 150                 155                 160

Ser Gly Gly Gly Gly Ser Gln Pro Val Leu Thr Gln Ser Ser Ser Leu
                165                 170                 175

Ser Ala Ser Pro Gly Ala Ser Ala Ser Leu Thr Cys Thr Leu Arg Ser
            180                 185                 190

Gly Ile Asn Val Gly Pro Tyr Arg Ile Tyr Trp Tyr Gln Gln Lys Pro
        195                 200                 205

Gly Ser Pro Pro Gln Tyr Leu Leu Asn Tyr Lys Ser Asp Ser Asp Lys
    210                 215                 220

Gln Gln Gly Ser Gly Val Pro Ser Arg Phe Ser Gly Ser Lys Asp Ala
225                 230                 235                 240

Ser Ala Asn Ala Gly Val Leu Leu Ile Ser Gly Leu Arg Ser Glu Asp
                245                 250                 255

Glu Ala Asp Tyr Tyr Cys Met Ile Trp His Ser Ser Ala Ala Val Phe
            260                 265                 270

Gly Gly Gly Thr Gln Leu Thr Val Leu Ser Ala Ser Thr Thr Thr Pro
        275                 280                 285

Ala Pro Arg Pro Pro Thr Pro Ala Pro Thr Ile Ala Ser Gln Pro Leu

Ser Leu Arg Pro Glu Ala Cys Arg Pro Ala Ala Gly Gly Ala Val His
305                 310                 315                 320

Thr Arg Gly Leu Asp Phe Ala Cys Asp Phe Trp Val Leu Val Val Val
                325                 330                 335

Gly Gly Val Leu Ala Cys Tyr Ser Leu Leu Val Thr Val Ala Phe Ile
            340                 345                 350

Ile Phe Trp Val Arg Ser Lys Arg Ser Arg Leu Leu His Ser Asp Tyr
        355                 360                 365

Met Asn Met Thr Pro Arg Arg Pro Gly Pro Thr Arg Lys His Tyr Gln
    370                 375                 380

Pro Tyr Ala Pro Pro Arg Asp Phe Ala Ala Tyr Arg Ser Ile Asp Arg
385                 390                 395                 400

Val Lys Phe Ser Arg Ser Ala Asp Ala Pro Ala Tyr Gln Gln Gly Gln
                405                 410                 415

Asn Gln Leu Tyr Asn Glu Leu Asn Leu Gly Arg Arg Glu Glu Tyr Asp
            420                 425                 430

Val Leu Asp Lys Arg Arg Gly Arg Asp Pro Glu Met Gly Gly Lys Pro
        435                 440                 445

Arg Arg Lys Asn Pro Gln Glu Gly Leu Tyr Asn Glu Leu Gln Lys Asp
    450                 455                 460

Lys Met Ala Glu Ala Tyr Ser Glu Ile Gly Met Lys Gly Glu Arg Arg
465                 470                 475                 480

Arg Gly Lys Gly His Asp Gly Leu Tyr Gln Gly Leu Ser Thr Ala Thr
                485                 490                 495

Lys Asp Thr Tyr Asp Ala Leu His Met Gln Ala Leu Pro Pro Arg
            500                 505                 510

<210> SEQ ID NO 6
<211> LENGTH: 1536
<212> TYPE: DNA
<213> ORGANISM: Artificial
<220> FEATURE:
<223> OTHER INFORMATION: Chemcially synthesized

<400> SEQUENCE: 6
atggccttac cagtgaccgc cttgctcctg ccgctggcct tgctgctcca cgccgccagg      60
ccgggatctc aggtacagct gcagcagtca ggtccaggac tcgtgacgcc ctcgcagacc     120
ctctcactca cctgtgccat ctccggggac agtgtctcta gcaacagtgc tacttggaac     180
tggatcaggc agtccccatc gagaggcctt gagtggctgg aaggacata ctacaggtcc      240 aagtggtata cgactatgc agtatctgtg aaaagtcgaa tgagcatcaa cccagacaca      300
tccaagaacc agttctccct gcagctgaac tctgtgactc ccgaggacac ggctgtgtat     360
tactgtgcaa gaggaatgat gacttactat acggtatgg acgtctgggg ccaagggacc      420
acggtcaccg tctcctcagg aattctagga tccgtggcg gtggcagcgg cggtggtggt     480
tccggaggcg gcggttctca gcctgtgctg actcagtcgt cttccctctc tgcatctcct     540
ggagcatcag ccagtctcac ctgcaccttg cgcagtggca tcaatgttgg tccctacagg     600
atatactggt accagcagaa gccagggagt cctccccagt atctcctgaa ctacaaatca     660
gactcagata gcagcaggg ctctggagtc cccagccgct ctctggatc caaagatgct      720 tcggccaatg caggggtttt actcatctct gggctccgt ctgaggatga ggctgactat     780
tactgtatga tttggcacag cagcgctgct gtgttcggag gaggcaccca actgaccgtc     840

```
ctctccgcta gcaccacgac gccagcgccg cgaccaccaa caccggcgcc caccatcgcg    900
tcgcagcccc tgtccctgcg cccagaggcg tgccggccag cggcgggggg cgcagtgcac    960
acgagggggc tggacttcgc ctgtgatttt tgggtgctgg tggtggttgg tggagtcctg   1020
gcttgctata gcttgctagt aacagtggcc tttattattt tctgggtgag gagtaagagg   1080
agcaggctcc tgcacagtga ctacatgaac atgactcccc gccgcccgg gcccacccgc    1140 aagcattacc agccctatgc cccaccacgc gacttcgcag cctatcgctc catcgataga   1200
gtgaagttca gcaggagcgc agacgccccc gcgtaccagc agggccagaa ccagctctat   1260
aacgagctca atctaggacg aagagaggag tacgatgttt tggacaagag acgtggccgg   1320
gaccctgaga tggggggaaa gccgagaagg aagaaccctc aggaaggcct gtacaatgaa   1380
ctgcagaaag ataagatggc ggaggcctac agtgagattg ggatgaaagg cgagcgccgg   1440
aggggcaagg ggcacgatgg cctttaccag ggtctcagta cagccaccaa ggacacctac   1500
gacgcccttc acatgcaggc cctgccccct cgctaa                             1536
```

<210> SEQ ID NO 7
<211> LENGTH: 507
<212> TYPE: PRT
<213> ORGANISM: Artificial
<220> FEATURE:
<223> OTHER INFORMATION: Chemically synthesized

<400> SEQUENCE: 7

```
Met Ala Leu Pro Val Thr Ala Leu Leu Leu Pro Leu Ala Leu Leu Leu
1               5                   10                  15

His Ala Ala Arg Pro Gly Ser Gln Val Gln Leu Gln Gln Ser Gly Pro
            20                  25                  30

Gly Leu Val Thr Pro Ser Gln Thr Leu Ser Leu Thr Cys Ala Ile Ser
        35                  40                  45

Gly Asp Ser Val Ser Ser Asn Ser Ala Thr Trp Asn Trp Ile Arg Gln
    50                  55                  60

Ser Pro Ser Arg Gly Leu Glu Trp Leu Gly Arg Thr Tyr Tyr Arg Ser
65                  70                  75                  80

Lys Trp Tyr Asn Asp Tyr Ala Val Ser Val Lys Ser Arg Met Ser Ile
                85                  90                  95

Asn Pro Asp Thr Ser Lys Asn Gln Phe Ser Leu Gln Leu Asn Ser Val
            100                 105                 110

Thr Pro Glu Asp Thr Ala Val Tyr Tyr Cys Ala Arg Gly Met Met Thr
        115                 120                 125

Tyr Tyr Tyr Gly Met Asp Val Trp Gly Gln Gly Thr Thr Val Thr Val
    130                 135                 140

Ser Ser Gly Ile Leu Gly Ser Gly Gly Gly Ser Gly Gly Gly Gly
145                 150                 155                 160

Ser Gly Gly Gly Gly Ser Gln Pro Val Leu Thr Gln Ser Ser Ser Leu
                165                 170                 175

Ser Ala Ser Pro Gly Ala Ser Ala Ser Leu Thr Cys Thr Leu Arg Ser
            180                 185                 190

Gly Ile Asn Val Gly Pro Tyr Arg Ile Tyr Trp Tyr Gln Gln Lys Pro
        195                 200                 205

Gly Ser Pro Pro Gln Tyr Leu Leu Asn Tyr Lys Ser Asp Ser Asp Lys
    210                 215                 220

Gln Gln Gly Ser Gly Val Pro Ser Arg Phe Ser Gly Ser Lys Asp Ala
225                 230                 235                 240
```

Ser Ala Asn Ala Gly Val Leu Leu Ile Ser Gly Leu Arg Ser Glu Asp
            245                 250                 255

Glu Ala Asp Tyr Tyr Cys Met Ile Trp His Ser Ser Ala Ala Val Phe
        260                 265                 270

Gly Gly Gly Thr Gln Leu Thr Val Leu Ser Ala Ser Thr Thr Thr Pro
    275                 280                 285

Ala Pro Arg Pro Pro Thr Pro Ala Pro Thr Ile Ala Ser Gln Pro Leu
290                 295                 300

Ser Leu Arg Pro Glu Ala Cys Arg Pro Ala Ala Gly Gly Ala Val His
305                 310                 315                 320

Thr Arg Gly Leu Asp Phe Ala Cys Asp Ile Tyr Ile Trp Ala Pro Leu
            325                 330                 335

Ala Gly Thr Cys Gly Val Leu Leu Leu Ser Leu Val Ile Thr Leu Tyr
        340                 345                 350

Cys Lys Arg Gly Arg Lys Lys Leu Leu Tyr Ile Phe Lys Gln Pro Phe
    355                 360                 365

Met Arg Pro Val Gln Thr Thr Gln Glu Glu Asp Gly Cys Ser Cys Arg
370                 375                 380

Phe Pro Glu Glu Glu Glu Gly Gly Cys Glu Leu Arg Val Lys Phe Ser
385                 390                 395                 400

Arg Ser Ala Asp Ala Pro Ala Tyr Lys Gln Gly Gln Asn Gln Leu Tyr
            405                 410                 415

Asn Glu Leu Asn Leu Gly Arg Arg Glu Glu Tyr Asp Val Leu Asp Lys
        420                 425                 430

Arg Arg Gly Arg Asp Pro Glu Met Gly Gly Lys Pro Arg Arg Lys Asn
    435                 440                 445

Pro Gln Glu Gly Leu Tyr Asn Glu Leu Gln Lys Asp Lys Met Ala Glu
450                 455                 460

Ala Tyr Ser Glu Ile Gly Met Lys Gly Glu Arg Arg Arg Gly Lys Gly
465                 470                 475                 480

His Asp Gly Leu Tyr Gln Gly Leu Ser Thr Ala Thr Lys Asp Thr Tyr
            485                 490                 495

Asp Ala Leu His Met Gln Ala Leu Pro Pro Arg
        500                 505

<210> SEQ ID NO 8
<211> LENGTH: 1524
<212> TYPE: DNA
<213> ORGANISM: Artificial
<220> FEATURE:
<223> OTHER INFORMATION: Chemically synthesized

<400> SEQUENCE: 8
atggccttac cagtgaccgc cttgctcctg ccgctggcct tgctgctcca cgccgccagg     60
ccgggatctc aggtacagct gcagcagtca ggtccaggac tcgtgacgcc ctcgcagacc    120
ctctcactca cctgtgccat ctccggggac agtgtctcta gcaacagtgc tacttggaac    180
tggatcaggc agtccccatc gagaggcctt gagtggctgg aaggacata ctacaggtcc    240 aagtggtata cgactatgc agtatctgtg aaaagtcgaa tgagcatcaa cccagacaca    300
tccaagaacc agttctccct gcagctgaac tctgtgactc ccgaggacac ggctgtgtat    360
tactgtgcaa aggaatgat gacttactat acggtatgg acgtctgggg ccaagggacc    420
acggtcaccg tctcctcagg aattctagga tccggtggcg gtggcagcgg cggtggtggt    480
tccggaggcg gcggttctca gcctgtgctg actcagtcgt cttccctctc tgcatctcct    540

```
ggagcatcag ccagtctcac ctgcaccttg cgcagtggca tcaatgttgg tccctacagg    600
atatactggt accagcagaa gccagggagt cctccccagt atctcctgaa ctacaaatca    660
gactcagata agcagcaggg ctctggagtc cccagccgct tctctggatc caaagatgct    720
tcggccaatg cagggttttt actcatctct gggctccggt ctgaggatga ggctgactat    780
tactgtatga tttggcacag cagcgctgct gtgttcggag gaggcaccca actgaccgtc    840
ctctccgcta gcaccacgac gccagcgccg cgaccaccaa caccggcgcc caccatcgcg    900
tcgcagcccc tgtccctgcg cccagaggcg tgccggccag cggcgggggg cgcagtgcac    960 acgaggggc tggacttcgc ctgtgatatc tacatctggg cgcccttggc cgggacttgt     1020
ggggtccttc tcctgtcact ggttatcacc ctttactgca aacggggcag aaagaaactc    1080
ctgtatatat tcaaacaacc atttatgaga ccagtacaaa ctactcaaga ggaagatggc    1140
tgtagctgcc gatttccaga agaagaagaa ggaggatgtg aactgagagt gaagttcagc    1200
aggagcgcag acgccccgc gtacaagcag ggccagaacc agctctataa cgagctcaat     1260
ctaggacgaa gagaggagta cgatgttttg acaagagac gtggccggga ccctgagatg      1320
gggggaaagc cgagaaggaa gaaccctcag gaaggcctgt acaatgaact gcagaaagat    1380
aagatggcgg aggcctacag tgagattggg atgaaaggcg agcgccggag gggcaagggg    1440
cacgatggcc tttaccaggg tctcagtaca gccaccaagg acacctacga cgcccttcac    1500
atgcaggccc tgccccctcg ctaa                                           1524
```

```
<210> SEQ ID NO 9
<211> LENGTH: 34
<212> TYPE: PRT
<213> ORGANISM: Artificial
<220> FEATURE:
<223> OTHER INFORMATION: Chemically synthesized

<400> SEQUENCE: 9

Met Ala Leu Pro Val Thr Ala Leu Leu Leu Pro Leu Ala Leu Leu Leu
1               5                   10                  15

His Ala Ala Arg Pro Gly Ser Gln Val Gln Leu Gln Gln Ser Gly Pro
            20                  25                  30

Gly Leu

<210> SEQ ID NO 10
<211> LENGTH: 63
<212> TYPE: DNA
<213> ORGANISM: Artificial
<220> FEATURE:
<223> OTHER INFORMATION: Chemically synthesized

<400> SEQUENCE: 10
atggccttac cagtgaccgc cttgctcctg ccgctggcct tgctgctcca cgccgccagg    60
ccg                                                                  63

<210> SEQ ID NO 11
<211> LENGTH: 259
<212> TYPE: PRT
<213> ORGANISM: Artificial
<220> FEATURE:
<223> OTHER INFORMATION: Chemcially synthesized

<400> SEQUENCE: 11

Gln Val Gln Leu Gln Gln Ser Gly Pro Gly Leu Val Thr Pro Ser Gln
1               5                   10                  15
```

Thr Leu Ser Leu Thr Cys Ala Ile Ser Gly Asp Ser Val Ser Ser Asn
                20                  25                  30

Ser Ala Thr Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
        50                  55                  60

Val Ser Val Lys Ser Arg Met Ser Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Met Met Thr Tyr Tyr Gly Met Asp Val
            100                 105                 110

Trp Gly Gln Gly Thr Thr Val Thr Val Ser Ser Gly Ile Leu Gly Ser
        115                 120                 125

Gly Gly Gly Gly Ser Gly Gly Gly Ser Gly Gly Gly Ser Gln
130                 135                 140

Pro Val Leu Thr Gln Ser Ser Ser Leu Ser Ala Ser Pro Gly Ala Ser
145                 150                 155                 160

Ala Ser Leu Thr Cys Thr Leu Arg Ser Gly Ile Asn Val Gly Pro Tyr
                165                 170                 175

Arg Ile Tyr Trp Tyr Gln Gln Lys Pro Gly Ser Pro Pro Gln Tyr Leu
            180                 185                 190

Leu Asn Tyr Lys Ser Asp Ser Asp Lys Gln Gln Gly Ser Gly Val Pro
        195                 200                 205

Ser Arg Phe Ser Gly Ser Lys Asp Ala Ser Ala Asn Ala Gly Val Leu
210                 215                 220

Leu Ile Ser Gly Leu Arg Ser Glu Asp Glu Ala Asp Tyr Tyr Cys Met
225                 230                 235                 240

Ile Trp His Ser Ser Ala Ala Val Phe Gly Gly Gly Thr Gln Leu Thr
                245                 250                 255

Val Leu Ser

<210> SEQ ID NO 12
<211> LENGTH: 777
<212> TYPE: DNA
<213> ORGANISM: Artificial
<220> FEATURE:
<223> OTHER INFORMATION: Chemically synthesized

<400> SEQUENCE: 12
caggtacagc tgcagcagtc aggtccagga ctcgtgacgc cctcgcagac cctctcactc      60
acctgtgcca tctccgggga cagtgtctct agcaacagtg ctacttggaa ctggatcagg     120
cagtccccat cgagaggcct tgagtggctg gaaggacat actacaggtc caagtggtat      180
aacgactatg cagtatctgt gaaaagtcga atgagcatca cccagacac atccaagaac      240 cagttctccc tgcagctgaa ctctgtgact cccgaggaca cggctgtgta ttactgtgca     300
agaggaatga tgacttacta ttacggtatg gacgtctggg gccaagggac cacggtcacc     360
gtctcctcag gaattctagg atccggtggc ggtggcagcg gcggtggtgg ttccggaggc     420
ggcggttctc agcctgtgct gactcagtcg tcttccctct ctgcatctcc tggagcatca     480
gccagtctca cctgcaccct gcgcagtggc atcaatgttg gtccctacag gatatactgg     540
taccagcaga agccagggag tcctccccag tatctcctga actacaaatc agactcagat     600
aagcagcagg gctctggagt cccagccgc ttctctggat ccaaagatgc ttcggccaat     660

```
gcaggggttt tactcatctc tgggctccgg tctgaggatg aggctgacta ttactgtatg    720
atttggcaca gcagcgctgc tgtgttcgga ggaggcaccc aactgaccgt cctctcc       777
```

<210> SEQ ID NO 13
<211> LENGTH: 45
<212> TYPE: PRT
<213> ORGANISM: Artificial
<220> FEATURE:
<223> OTHER INFORMATION: Chemically synthesized

<400> SEQUENCE: 13

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

<210> SEQ ID NO 14
<211> LENGTH: 134
<212> TYPE: DNA
<213> ORGANISM: Artificial
<220> FEATURE:
<223> OTHER INFORMATION: Chemically synthesized

<400> SEQUENCE: 14

```
accacgacgc cagcgccgcg accaccaaca ccggcgccca ccatcgcgtc gcagcccctg    60
tccctgcgcc agaggcgtg ccggccagcg gcggggggcg cagtgcacac gagggggctg    120
gacttcgcct gtga                                                     134
```

<210> SEQ ID NO 15
<211> LENGTH: 27
<212> TYPE: PRT
<213> ORGANISM: Artificial
<220> FEATURE:
<223> OTHER INFORMATION: Chemically synthesized

<400> SEQUENCE: 15

```
Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

<210> SEQ ID NO 16
<211> LENGTH: 81
<212> TYPE: DNA
<213> ORGANISM: Artificial
<220> FEATURE:
<223> OTHER INFORMATION: Chemically synthesized

<400> SEQUENCE: 16

```
ttttgggtgc tggtggtggt tgtggagtc ctggcttgct atagcttgct agtaacagtg    60
gcctttatta ttttctgggt g                                             81
```

<210> SEQ ID NO 17
<211> LENGTH: 24
<212> TYPE: PRT
<213> ORGANISM: Artificial
<220> FEATURE:
<223> OTHER INFORMATION: Chemically synthesized

<400> SEQUENCE: 17

```
Ile Tyr Ile Trp Ala Pro Leu Ala Gly Thr Cys Gly Val Leu Leu Leu
1               5                   10                  15

Ser Leu Val Ile Thr Leu Tyr Cys
            20
```

<210> SEQ ID NO 18
<211> LENGTH: 73
<212> TYPE: DNA
<213> ORGANISM: Artificial
<220> FEATURE:
<223> OTHER INFORMATION: Chemically synthesized

<400> SEQUENCE: 18

```
tatctacatc tgggcgccct tggccgggac ttgtggggtc cttctcctgt cactggttat    60
caccctttac tgc                                                       73
```

<210> SEQ ID NO 19
<211> LENGTH: 42
<212> TYPE: PRT
<213> ORGANISM: Artificial
<220> FEATURE:
<223> OTHER INFORMATION: Chemically synthesized

<400> SEQUENCE: 19

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 20
<211> LENGTH: 126
<212> TYPE: DNA
<213> ORGANISM: Artificial
<220> FEATURE:
<223> OTHER INFORMATION: Chemically synthesized

<400> SEQUENCE: 20

```
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126
```

<210> SEQ ID NO 21
<211> LENGTH: 41
<212> TYPE: PRT
<213> ORGANISM: Artificial
<220> FEATURE:
<223> OTHER INFORMATION: Chemically synthesized

<400> SEQUENCE: 21

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 22
<211> LENGTH: 123
<212> TYPE: DNA
<213> ORGANISM: Artificial

<220> FEATURE:
<223> OTHER INFORMATION: Chemically synthesized

<400> SEQUENCE: 22

```
aggagtaaga ggagcaggct cctgcacagt gactacatga acatgactcc ccgccgcccc      60
gggcccaccc gcaagcatta ccagccctat gccccaccac gcgacttcgc agcctatcgc     120
tcc                                                                   123
```

<210> SEQ ID NO 23
<211> LENGTH: 112
<212> TYPE: PRT
<213> ORGANISM: Artificial
<220> FEATURE:
<223> OTHER INFORMATION: Chemically synthesized

<400> SEQUENCE: 23

```
Arg Val Lys Phe Ser Arg Ser Ala Asp Ala Pro Ala Tyr Lys Gln Gly
 1               5                  10                  15
Gln Asn Gln Leu Tyr Asn Glu Leu Asn Leu Gly Arg Arg Glu Glu Tyr
            20                  25                  30
Asp Val Leu Asp Lys Arg Arg Gly Arg Asp Pro Glu Met Gly Gly Lys
        35                  40                  45
Pro Arg Arg Lys Asn Pro Gln Glu Gly Leu Tyr Asn Glu Leu Gln Lys
    50                  55                  60
Asp Lys Met Ala Glu Ala Tyr Ser Glu Ile Gly Met Lys Gly Glu Arg
65                  70                  75                  80
Arg Arg Gly Lys Gly His Asp Gly Leu Tyr Gln Gly Leu Ser Thr Ala
                85                  90                  95
Thr Lys Asp Thr Tyr Asp Ala Leu His Met Gln Ala Leu Pro Pro Arg
           100                 105                 110
```

<210> SEQ ID NO 24
<211> LENGTH: 336
<212> TYPE: DNA
<213> ORGANISM: Artificial
<220> FEATURE:
<223> OTHER INFORMATION: Chemically synthesized

<400> SEQUENCE: 24

```
agagtgaagt tcagcaggag cgcagacgcc cccgcgtaca agcagggcca gaaccagctc      60
tataacgagc tcaatctagg acgaagagag gagtacgatg ttttggacaa gagacgtggc     120
cgggaccctg agatgggggg aaagccgaga aggaagaacc ctcaggaagg cctgtacaat     180
gaactgcaga agataagat ggcggaggcc tacagtgaga ttgggatgaa aggcgagcgc      240
cggaggggca aggggcacga tggcctttac cagggtctca gtacagccac caaggacacc     300
tacgacgccc ttcacatgca ggccctgccc cctcgc                               336
```